(12) United States Patent
Guzman et al.

(10) Patent No.: US 10,327,784 B2
(45) Date of Patent: Jun. 25, 2019

(54) METHOD FOR CUTTING BONE DURING AN ORTHOPAEDIC SURGICAL PROCEDURE

(71) Applicant: DePuy Synthes Products, Inc., Raynham, MA (US)

(72) Inventors: Jose F. Guzman, Fort Wayne, IN (US); Gordon Dodds, Feldkirchen (DE)

(73) Assignee: DePuy Synthes Products, Inc., Raynham, MA (US)

( * ) Notice: Subject to any disclaimer, the term of this patent is extended or adjusted under 35 U.S.C. 154(b) by 676 days.

(21) Appl. No.: 14/103,186

(22) Filed: Dec. 11, 2013

(65) Prior Publication Data

US 2014/0100577 A1 Apr. 10, 2014

Related U.S. Application Data

(62) Division of application No. 12/048,880, filed on Mar. 14, 2008, now Pat. No. 8,608,745.

(60) Provisional application No. 60/908,035, filed on Mar. 26, 2007.

(51) Int. Cl.
*A61B 17/14* (2006.01)
*A61B 17/15* (2006.01)
*A61B 90/00* (2016.01)

(52) U.S. Cl.
CPC .......... *A61B 17/142* (2016.11); *A61B 17/157* (2013.01); *A61B 2090/0801* (2016.02)

(58) Field of Classification Search
CPC ..... A61B 17/14; A61B 17/148; A61B 17/157; A61B 2019/4805
See application file for complete search history.

(56) References Cited

U.S. PATENT DOCUMENTS

| | | | |
|---|---|---|---|
| 1,095,399 A | | 5/1914 | Huntington |
| 1,308,798 A | * | 7/1919 | Masland ............ A61B 17/1617 279/9.1 |
| 1,375,698 A | | 4/1921 | Howe |
| 1,685,213 A | | 2/1925 | Boyce |
| 2,455,655 A | * | 12/1948 | Carroll ................... A61B 17/14 30/372 |
| 2,702,550 A | * | 2/1955 | Rowe ..................... A61B 17/14 606/178 |
| 3,905,105 A | | 9/1975 | Tuke |
| 3,974,724 A | | 8/1976 | Shadle |
| 3,977,289 A | | 8/1976 | Tuke |
| 4,280,276 A | * | 7/1981 | Comer .................. A01G 3/053 30/144 |
| 4,297,928 A | | 11/1981 | Benuzzi |

(Continued)

FOREIGN PATENT DOCUMENTS

| | | | |
|---|---|---|---|
| DE | 102007007915 | * | 8/2008 |
| EP | 0695607 | | 2/1996 |
| JP | 2004254629 | | 9/2004 |

OTHER PUBLICATIONS

European Search Report for European Patent Application No. 08251049.6-2310/1974679, dated Oct. 28, 2008, 9 pgs.

*Primary Examiner* — Zade Coley
(74) *Attorney, Agent, or Firm* — Barnes & Thornburg LLP

(57) ABSTRACT

A method for cutting a bone of a patient using a bone saw tool that includes determining a cutting region that corresponds to a region of the bone to be cut and determining the position of the bone saw tool in the coordinate system. The method includes activating a bone saw blade guard of the bone saw tool if the bone saw tool is outside the cutting region.

9 Claims, 28 Drawing Sheets

(56) References Cited

U.S. PATENT DOCUMENTS

| | | | |
|---|---|---|---|
| 4,461,296 A * | 7/1984 | Hodge | A61B 17/14 30/347 |
| 4,718,413 A * | 1/1988 | Johnson | A61B 17/157 606/82 |
| 4,776,095 A * | 10/1988 | Tsujimoto | B26B 19/20 30/201 |
| 5,105,541 A * | 4/1992 | Messinger | B26B 19/20 30/200 |
| 5,122,142 A * | 6/1992 | Pascaloff | A61B 17/14 606/171 |
| 5,263,972 A * | 11/1993 | Evans | A61B 17/14 30/339 |
| 5,306,285 A | 4/1994 | Miller et al. | |
| 5,382,249 A * | 1/1995 | Fletcher | A61B 17/14 606/176 |
| 5,403,318 A * | 4/1995 | Boehringer | A61B 17/14 606/178 |
| 5,423,825 A * | 6/1995 | Levine | A61B 17/1604 29/275 |
| D361,029 S * | 8/1995 | Goris | D24/146 |
| 5,571,100 A | 11/1996 | Goble et al. | |
| 5,662,661 A | 9/1997 | Boudjema | |
| 5,733,289 A * | 3/1998 | Seedhom | A61B 17/1677 606/80 |
| 5,735,866 A | 4/1998 | Adams et al. | |
| 6,097,168 A * | 8/2000 | Katoh | 318/560 |
| 6,113,618 A * | 9/2000 | Nic | A61B 17/14 30/351 |
| 6,189,560 B1 | 2/2001 | Reynolds | |
| 6,283,971 B1 * | 9/2001 | Temeles | A61B 17/1666 606/79 |
| 6,302,406 B1 | 10/2001 | Ventura | |
| 6,757,582 B2 * | 6/2004 | Brisson | A61B 19/20 606/128 |
| 6,875,222 B2 * | 4/2005 | Long | A61B 17/14 30/374 |
| 6,949,110 B2 | 9/2005 | Ark et al. | |
| 7,022,123 B2 | 4/2006 | Heldreth | |
| 7,691,106 B2 | 4/2010 | Schenberger et al. | |
| 7,744,616 B2 | 6/2010 | O'Donoghue | |
| 2003/0176867 A1 | 9/2003 | Long et al. | |
| 2003/0208296 A1 * | 11/2003 | Brisson | A61B 34/20 700/117 |
| 2004/0034302 A1 * | 2/2004 | Abovitz | A61B 19/2203 600/428 |
| 2004/0215197 A1 * | 10/2004 | Smith | A61B 17/1671 606/79 |
| 2005/0119783 A1 * | 6/2005 | Brisson | A61B 19/20 700/186 |
| 2005/0228256 A1 * | 10/2005 | Labadie | A61B 19/52 600/407 |
| 2005/0273109 A1 * | 12/2005 | Bjork | A61B 17/1626 606/80 |
| 2006/0009796 A1 * | 1/2006 | Carusillo | A61B 17/14 606/178 |
| 2006/0156877 A1 | 7/2006 | Plonsky et al. | |
| 2007/0083209 A1 | 4/2007 | Schenberger et al. | |
| 2007/0119055 A1 | 5/2007 | Walen et al. | |

* cited by examiner

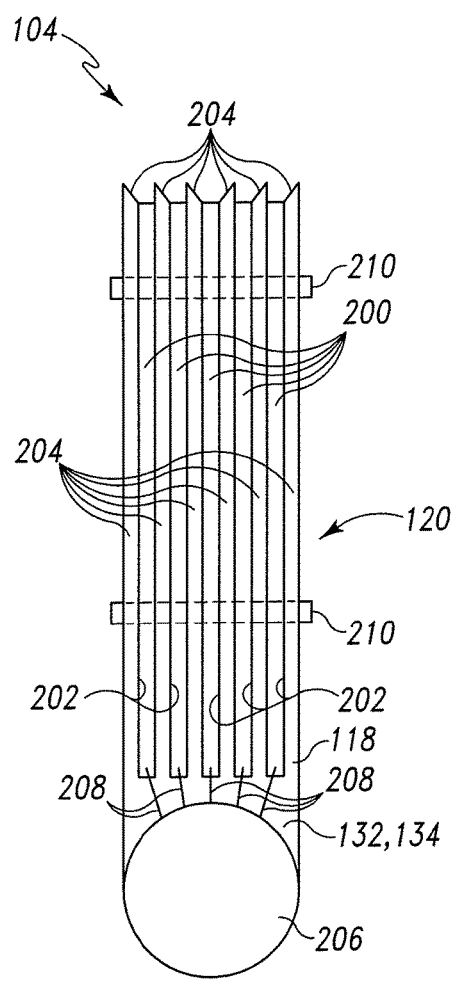
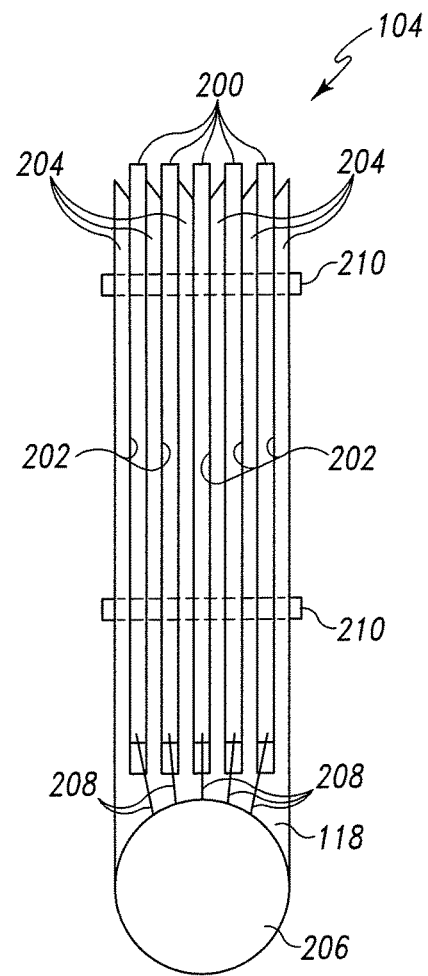
Fig. 20   Fig. 21
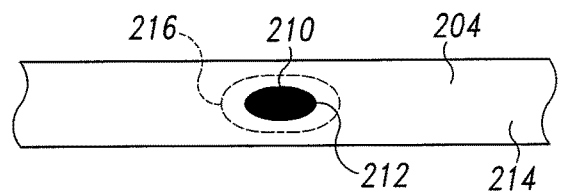
Fig. 22

METHOD FOR CUTTING BONE DURING AN
ORTHOPAEDIC SURGICAL PROCEDURE

This patent application is a divisional application of U.S. patent application Ser. No. 12/048,880, now U.S. Pat. No. 8,608,745, which was filed on Mar. 14, 2008, and claims priority to and the benefit of U.S. Provisional Patent Application Ser. No. 60/908,035 entitled "System, Apparatus, And Method For Cutting Bone During An Orthopaedic Surgical Procedure" by Jose F. Guzman, which was filed on Mar. 26, 2007. Those applications are expressly incorporated in their entirety by reference into this application.

TECHNICAL FIELD

The present disclosure relates generally to orthopaedic surgical tools used to cut and/or resect a bone of a patient during an orthopaedic surgical procedure such as, for example, a joint replacement procedure. Specifically, the present disclosure relates to bone saws and bone saw blades.

BACKGROUND

Orthopaedic surgical procedures often involve cutting, trimming, drilling, and/or shaving of bone structures such as long bones and/or joint-type bones. Long bones are hard, dense bones that generally provide strength, structure, and mobility. Long bones include the femur, tibia, and fibula of the leg, the humerus, radius, and ulna of the arm, and the phalange of the finger and toe, for example. Oscillating bone saws are oftentimes used to prepare such bones to receive and properly align an orthopaedic implant during various orthopaedic surgical procedures such as total or partial joint replacement surgeries, for example, where some or all of an arthritic or damaged joint is replaced by an artificial joint. Exemplary bone saws can be found in U.S. Pat. Nos. 3,905,105; 3,977,289; 6,949,110; 6,302,406 and within U.S. Patent Publication No. US 2006/0009796.

Such bone structures are surrounded by soft tissue such as muscle, cartilage, tendons, and ligaments, for example. These soft tissue structures may be difficult to isolate during orthopaedic procedures which involve the cutting of bone structures. For example, surgeons use instruments such as retractors to move the soft tissue away from the operating site to provide both proper visualization of the bone and also to prevent any inadvertent damage to the soft tissue. However, the soft tissue remains attached to the bony structures and may only be retracted a finite amount. As such, the surrounding soft tissue may be unintentionally damaged by the oscillating bone saw during the orthopaedic surgical procedure.

SUMMARY

According to one aspect, a method for cutting a bone of a patient using a bone saw tool may include determining a cutting region within a coordinate system defined by a computer assisted orthopaedic surgery system. The cutting region may correspond to a region of the bone to be cut. The method may also include determining the position of the bone saw tool in the coordinate system. To do so, the bone saw tool may include a reference array. The method may also include activating a bone saw blade guard of the bone saw tool if the bone saw tool is outside the cutting region.

In some embodiments, the method may include transmitting a signal to the bone saw tool. In such embodiments, the saw blade guard may be activated in response to the signal. Additionally, activating the bone saw blade guard may include reducing the cutting effectiveness of a saw blade of the bone saw tool. For example, at least a portion of the cutting teeth of the bone saw blade may be covered with the bone saw blade guard. When activated, the bone saw blade guard may be moved in a direction substantially parallel to a bone saw blade of the bone saw tool.

In some embodiments, activating the bone saw blade guard may include advancing a slat such that the slat covers a portion of the cutting teeth of the bone saw blade. Additionally, in some embodiments, activating the bone saw blade guard may include advancing a first slat positioned over a first side of the bone saw blade such that the first slat covers a portion of the cutting teeth of the bone saw blade on the first side and advancing a second slat positioned over a second side of the bone saw blade such that the second slat covers a portion of the cutting teeth of the bone saw blade on the second side.

In other embodiments, activating the bone saw blade guard may include advancing a number of first slats positioned over a first side of the bone saw blade of the bone saw tool such that each of the number of slats covers a portion of the cutting teeth of the bone saw blade on the first side. Additionally, activating the bone saw blade guard may include advancing a number of second slats positioned over a second side of the bone saw blade such that each of the number of second slats covers a portion of the cutting teeth of the bone saw blade on the second side. The method may also further include the movement of a saw blade of the bone saw tool if the bone saw tool is outside the cutting region.

In additional embodiments, activating the bone saw blade guard may include extending a slat positioned in a slot defined in a bone saw blade between a first cutting tooth and a second cutting tooth of the bone saw blade. The slat may be coplanar with the blade. Additionally, activating the bone saw blade guard may include extending a rod positioned in an inner passageway defined in a bone saw blade. Activating the bone saw blade guard may also include extending a sleeve over a cutting end of a bone saw blade. Further, activating the bone saw blade guard may include reducing the depth at which a bone saw blade can cut. In some embodiments, activating the bone saw blade guard may include extending a first bumper confronting a first side of a bone saw blade to an extended position and extending a second bumper confronting a second side of a bone saw blade to an extended position. In such embodiments, the bone saw blade may periodically contact the first bumper and the second bumper during operation when the first bumper and second bumper are in the extended position.

According to another aspect, a bone saw blade assembly for use with a bone saw may include a bone saw blade and a bone saw guard coupled to the bone saw blade. The bone saw blade may include a mounting end configured to be coupled with a chuck of the bone saw and a cutting end having a number of cutting teeth. The bone saw blade guard may be coupled to the bone saw blade and movable with respect to the bone saw blade. For example, the bone saw blade guard may be movable in a direction that is substantially parallel with the bone saw blade. In some embodiments, the bone saw blade guard is movable to an extended position and reduces the cutting effectiveness of the saw blade when in the extended position. For example, the bone saw blade guard may cover a portion of the number of cutting teeth of the bone saw blade when in the extended position.

In some embodiments, the bone saw blade guard is embodied as a slat having a width at least equal to the width of the bone saw blade. Additionally or alternatively, the bone saw blade guard may be embodied as a number of slats movable to an extended position such that each of the number of slats covers a portion of the number of cutting teeth of the bone saw blade when in the extended position.

In some embodiments, the bone saw blade guard may be embodied as a first bone saw blade guard positioned on a first side of the bone saw blade and a second bone saw blade guard positioned on a second side of the bone saw blade. In such embodiments, each of the first bone saw blade guard and the second bone saw blade guard may be embodied as a slat having a width at least equal to the width of the bone saw blade. Additionally or alternatively, each of the first bone saw blade guard and the second bone saw blade guard may be embodied as a number of slats movable to an extended position such that each of the number of slats covers a portion of the number of cutting teeth of the bone saw blade when in the extended position. Additionally, in some embodiments, the bone saw blade guard may include a hub coupled to the bone saw blade guard and configured to be coupled to the bone saw, the hub being operable to move the bone saw blade guard.

Additionally, in some embodiments, the bone saw blade guard may include a plurality of slats coplanar with the bone saw blade. Each of the plurality of slats may be positioned in a corresponding slot defined in the bone saw blade and extend beyond an end of the bone saw blade when in the extended position. In some embodiments, each of the plurality of slats may include a rail protruding outwardly from a sidewall of the slat. In such embodiments, the rail may be received in a slot defined in a sidewall of an elongated cutting tooth of the bone saw blade. In additional embodiments, the bone saw blade guard may include a push rod coupled to the plurality of slats and positioned in an inner passageway defined in the bone saw blade. Additionally, in other embodiments, the bone saw blade guard may include a first bumper and a second bumper. The first bumper may be positioned toward a first side of the bone saw blade and the second bumper may be positioned toward a second side of the bone saw blade. The bone saw blade may periodically contact the first bumper and the second bumper during operation when the first bumper and the second bumper are in the extended position.

According to another aspect, a bone saw blade assembly for use with a bone saw may include a bone saw blade, an actuator coupled to the bone saw blade, and a rod operatively coupled to the actuator. The bone saw blade may include a mounting end configured to be coupled with a chuck of the bone saw and a cutting end having a number of cutting teeth. The rod may be movable by the actuator between a retracted and extended position. In such embodiments, the maximum cutting depth of the bone saw blade is selectively determined based on the position of the rod.

According to a further aspect, a system for assisting in the performance of an orthopaedic surgical procedure may include a bone saw, a bone saw blade assembly coupled to the bone saw, a processor, and a memory device electrically coupled to the processor. The bone saw blade assembly may include a bone saw blade and a bone saw blade guard. The bone saw blade guard may be movable with respect to the bone saw blade. The memory device may have stored therein a plurality of instructions that, when executed by the processor, cause the processor to determine the location of the bone saw. Additionally, the plurality of instructions may cause the processor to transmit a signal to the bone saw if the bone saw is outside a predetermined region. In such embodiments, the bone saw may be configured to activate the bone saw blade guard in response to the signal.

According to yet a further aspect, a method for cutting a bone of a patient using a bone saw tool may include transmitting signal to the bone saw tool. The method may also include activating a bone saw blade guard of the bone saw tool in response to the signal.

According to a further aspect, a method for cutting a bone of a patient using a bone saw tool may include determining a cutting region within a coordinate system defined by a computer assisted orthopaedic surgery system. The cutting region may correspond to a region of the bone to be cut. the method may also include determining the position of the bone saw tool in the coordinate system. Additionally, the method may include reducing the cutting effectiveness of the cutting teeth of a bone saw blade of the bone saw tool if the bone saw tool is outside the cutting region. Reducing the cutting effectiveness of the cutting teeth may include activating a bone saw blade guard. For example, activating a bone saw blade guard may include extending a plurality of slats positioned coplanar with the bone saw blade such that the plurality of slats extend beyond the cutting teeth of the bone saw blade. Additionally, reducing the cutting effectiveness of the cutting teeth may include altering the thickness of a bone saw blade assembly of the bone saw tool. Reducing the cutting effectiveness of the cutting teeth may also include reducing the depth to which the bone saw blade is able to penetrate the bone of the patient.

BRIEF DESCRIPTION OF THE DRAWINGS

The detailed description particularly refers to the following figures, in which:

FIG. 20 is a plan view of another embodiment of the bone saw blade assembly of the bone saw tool of FIG. 6 having a bone saw blade guard in a retracted position;

FIG. 21 is a plan view of the bone saw blade assembly of FIG. 20 having the bone saw blade guard in an extended position;

FIG. 22 is a sectional side elevation view of the bone saw blade assembly of FIG. 20;

DETAILED DESCRIPTION OF THE DRAWINGS

Figure 1:
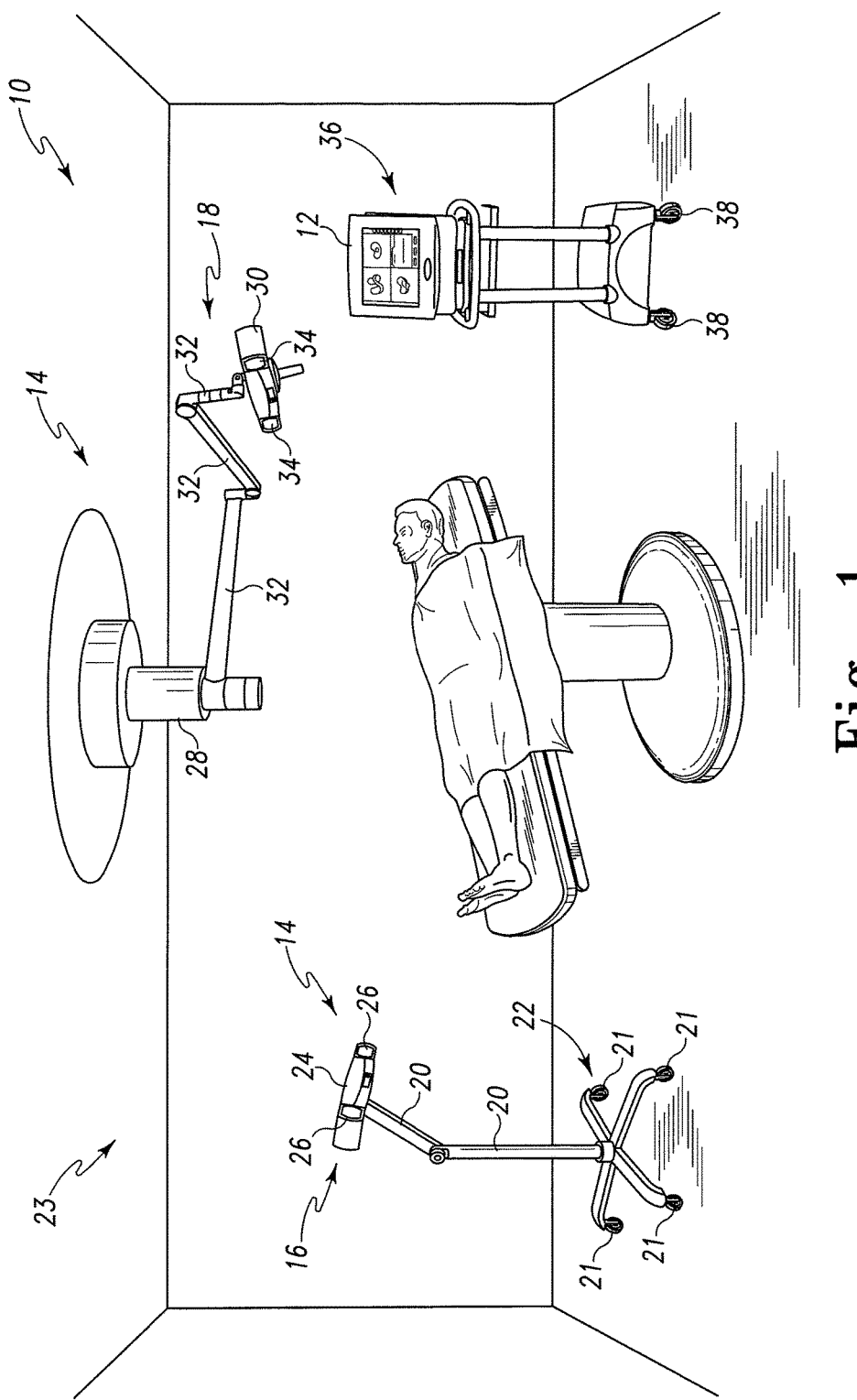
FIG. 1 is a perspective view of a computer assisted orthopaedic surgery (CAOS) system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a computer assisted orthopaedic surgery (CAOS) system 10 includes a computer 12 and a camera unit 14. The CAOS system 10 may be embodied as any type of computer assisted orthopaedic surgery system. Illustratively, the CAOS system 10 is embodied as one or more computer assisted orthopaedic surgery systems commercially available from DePuy Orthopaedics, Inc. of Warsaw, Ind. and/or one or more computer assisted orthopaedic surgery systems commercially available from BrainLAB of Heimstetten, Germany. The camera unit 14 may be embodied as a mobile camera unit 16 or a fixed camera unit 18. In some embodiments, the system 10 may include both types of camera units 16, 18. The mobile camera unit 16 includes a stand 20 coupled with a base 22. The base 22 may include a number of wheels 21 to allow the mobile camera unit 16 to be repositioned within a hospital room 23. The mobile camera unit 16 includes a camera head 24. The camera head 24 includes two cameras 26. The camera head 24 may be positionable relative to the stand 20 such that the field of view of the cameras 26 may be adjusted. The fixed camera unit 18 is similar to the mobile camera unit 16 and includes a base 28, a camera head 30, and an arm 32 coupling the camera head 30 with the base 28. In some embodiments, other peripherals, such as display screens, lights, and the like, may also be coupled with the base 28. The camera head 30 includes two cameras 34. The fixed camera unit 18 may be coupled to a ceiling, as illustratively shown in FIG. 1, or a wall of the hospital room. Similar to the camera head 24 of the camera unit 16, the camera head 30 may be positionable relative to the arm 32 such that the field of view of the cameras 34 may be adjusted. The camera units 14, 16, 18 are communicatively coupled with the computer 12. The computer 12 may be mounted on or otherwise coupled with a cart 36 having a number of wheels 38 to allow the computer 12 to be positioned near the surgeon during the performance of the orthopaedic surgical procedure.

Figure 2:
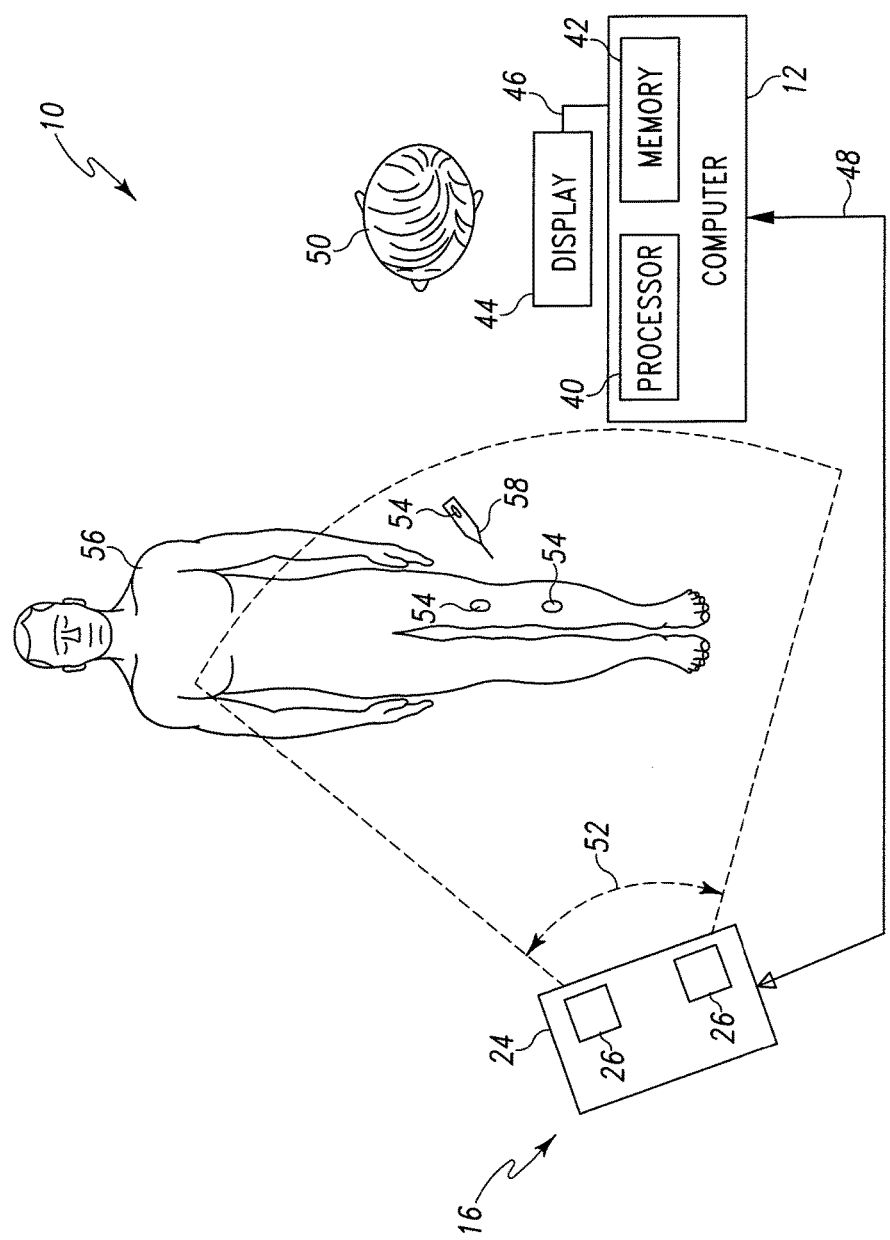
FIG. 2 is a simplified diagram of the CAOS system of FIG. 1.

Referring now to FIG. 2, the computer 12 illustratively includes a processor 40 and a memory device 42. The processor 40 may be embodied as any type of processor including, for example, discrete processing circuitry (e.g., a collection of logic devices), general purpose integrated circuit(s), and/or application specific integrated circuit(s) (i.e., ASICs). The memory device 42 may be embodied as any type of memory device and may include one or more memory types, such as, random access memory (i.e., RAM) and/or read-only memory (i.e., ROM). In addition, the computer 12 may include other devices and circuitry typically found in a computer for performing the functions described herein such as, for example, a hard drive, input/output circuitry, and the like.

The computer 12 is communicatively coupled with a display device 44 via a communication link 46. Although illustrated in FIG. 2 as separate from the computer 12, the display device 44 may form a portion of the computer 12 in some embodiments. Additionally, in some embodiments, the display device 44 or an additional display device may be positioned away from the computer 12. For example, the display device 44 may be coupled with the ceiling or wall of the operating room wherein the orthopaedic surgical procedure is to be performed. Additionally or alternatively, the display device 44 may be embodied as a virtual display such as a holographic display, a body mounted display such as a heads-up display, or the like. The computer 12 may also be coupled with a number of input devices such as a keyboard and/or a mouse for providing data input to the computer 12. However, in the illustrative embodiment, the display device 44 is a touch-screen display device capable of receiving inputs from an orthopaedic surgeon 50. That is, the surgeon 50 can provide input data to the computer 12, such as making a selection from a number of on-screen choices, by simply touching the screen of the display device 44.

The computer 12 is also communicatively coupled with the camera unit 16 (and/or 18) via a communication link 48. Illustratively, the communication link 48 is a wired communication link but, in some embodiments, may be embodied as a wireless communication link. In embodiments wherein the communication link 48 is a wireless signal path, the camera unit 16 and the computer 12 include wireless transceivers such that the computer 12 and camera unit 16 can transmit and receive data (e.g., image data). Although only the mobile camera unit 16 is shown in FIG. 2, it should be appreciated that the fixed camera unit 18 may alternatively be used or may be used in addition to the mobile camera unit 16.

Figure 3:
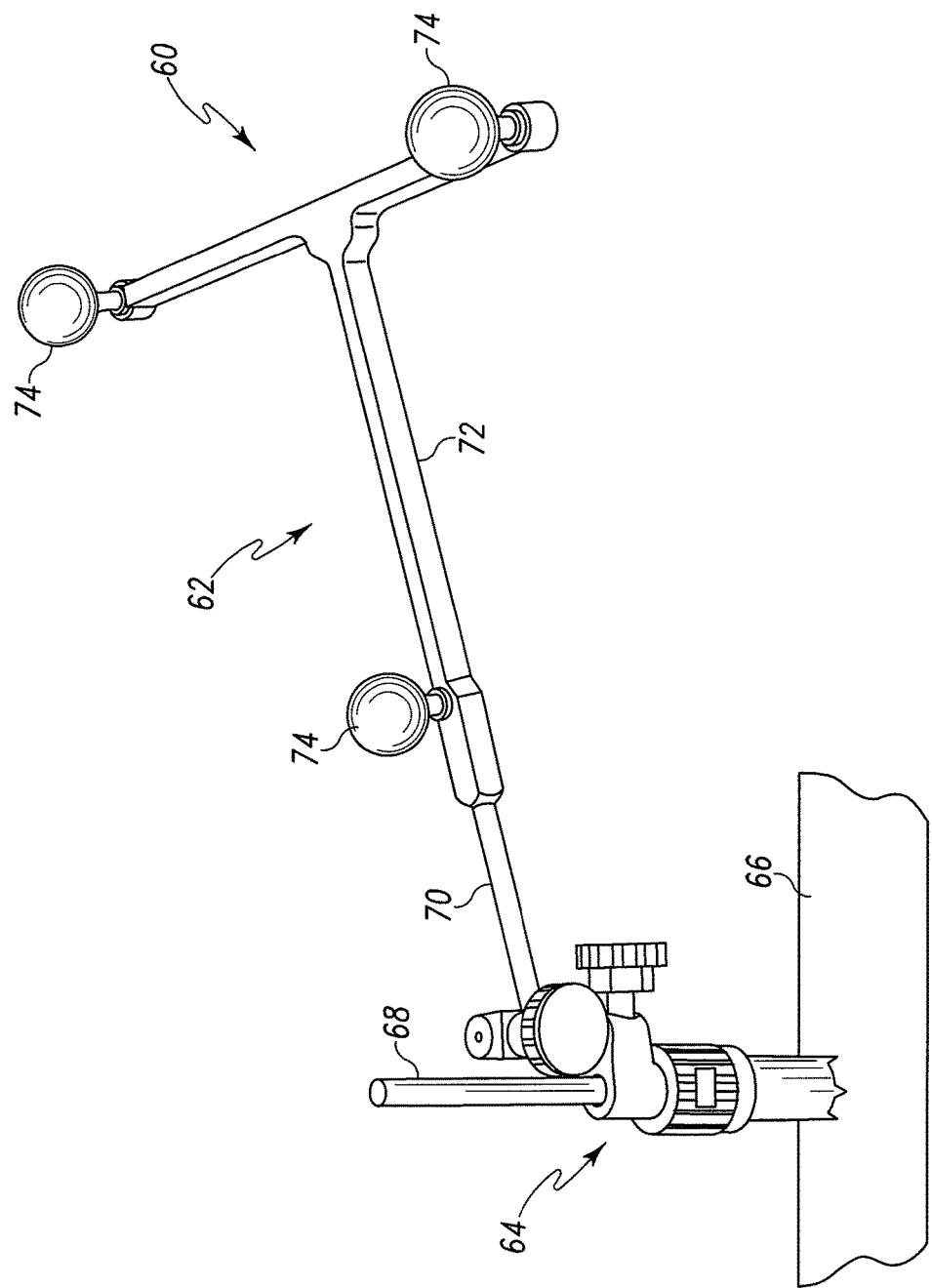
FIG. 3 is a perspective view of a bone locator tool.

The CAOS system 10 may also include a number of reference arrays 54 which may be coupled the relevant bones of a patient 56 and/or with one or more orthopaedic surgical tools 58. For example, as illustrated in FIG. 3, a tibial array 60 includes a reference array 62 and bone clamp 64. The illustrative bone clamp 64 is configured to be coupled with a tibia bone 66 of the patient 56 using a Schantz pin 68, but other types of bone clamps may be used. The reference array 62 is coupled with the bone clamp 64 via an extension arm 70. The reference array 62 includes a frame 72 and three reflective elements or sensors 74. The reflective elements 74 are embodied as spheres in the illustrative embodiment, but may have other geometric shapes in other embodiments. Additionally, in other embodiments reference arrays having more than three reflective elements may be used. The reflective elements 74 are positioned in a predefined configuration that allows the computer 12 to determine the identity of the tibial array 60 based on the configuration. That is, when the tibial array 60 is positioned in a field of view 52 of the camera head 24, as shown in FIG. 2, the computer 12 is configured to determine the identity of the tibial array 60 based on the images received from the camera head 24. Additionally, based on the relative position of the reflective elements 74, the computer 12 is configured to determine the location and orientation of the tibial array 60 and, accordingly, the tibia 66 to which the array 60 is coupled.

Figure 4:
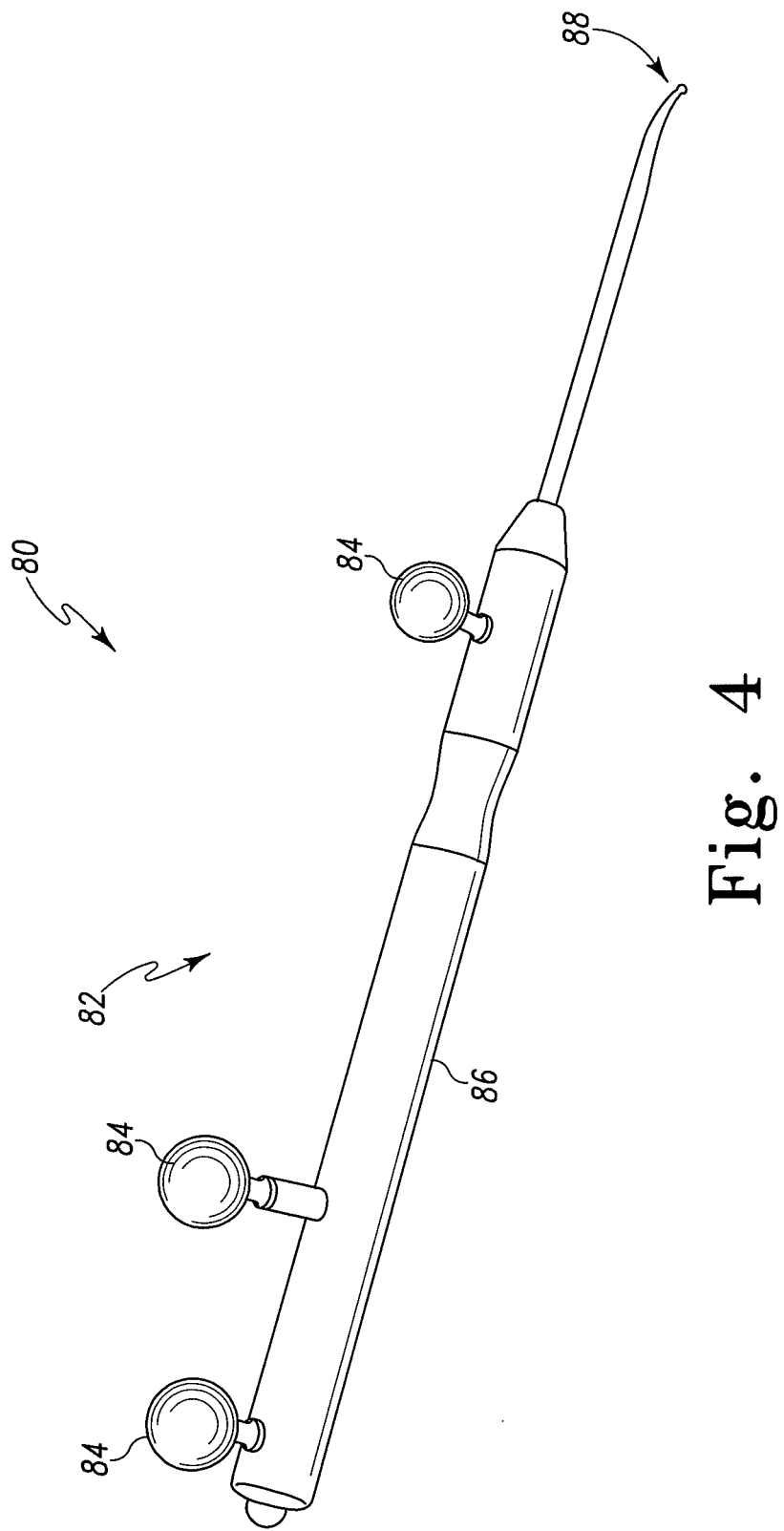
FIG. 4 is a perspective view of a registration tool for use with the system of FIG. 1.
Figure 5:
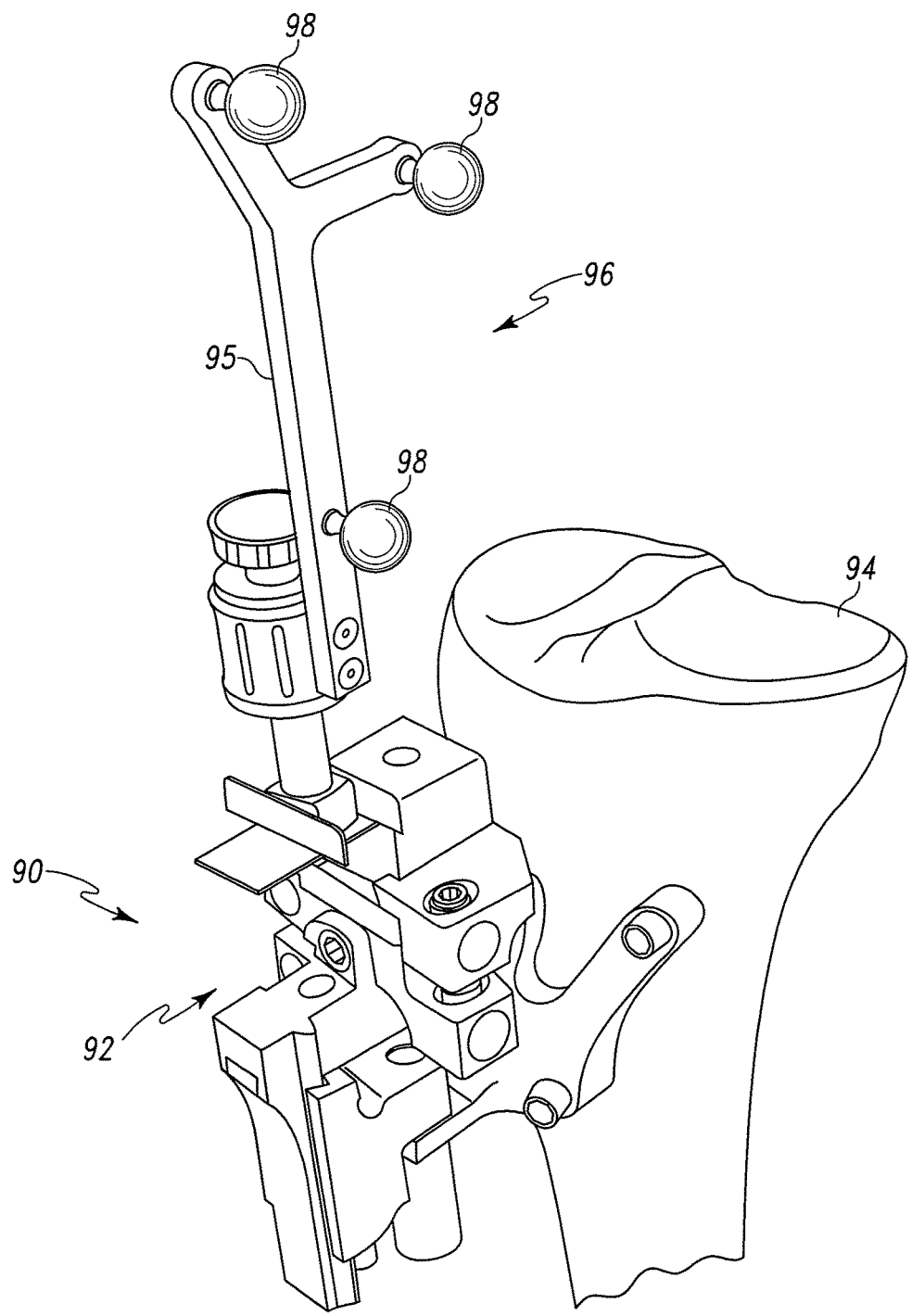
FIG. 5 is a perspective view of an orthopaedic surgical tool for use with the system of FIG. 1.

A reference array 54 may also be coupled to one or more orthopaedic surgical tools. For example, a registration tool 80, as shown in FIG. 4, is used to register points of a bone of the patient. The registration tool 80 includes a reference array 82 having three reflective elements 84 coupled with a handle 86 of the tool 80. The registration tool 80 also includes pointer end 88 that is used to register points of a bone. The reflective elements 84 are also positioned in a configuration that allows the computer 12 to determine the identity of the registration tool 80 and its relative location (i.e., the location of the pointer end 88). Additionally, reference arrays 54 may be used on other surgical tools such as a tibial resection jig 90, as illustrated in FIG. 5. The jig 90 includes a resection guide portion 92 that is coupled with a tibia bone 94 at a location of the bone 94 that is to be resected. The jig 90 includes a reference array 96 that is coupled with the portion 92 via a frame 95. The reference array 96 includes three reflective elements 98 that are positioned in a configuration that allows the computer 12 to determine the identity of the jig 90 and its relative location (e.g., with respect to the tibia bone 94).

The CAOS system 10 may be used by the orthopaedic surgeon 50 to assist in any type of orthopaedic surgical procedure including, for example, a total knee replacement procedure. To do so, the computer 12 and/or the display device 44 are positioned within the view of the surgeon 50. As discussed above, the computer 12 may be coupled with a movable cart 36 to facilitate such positioning. The camera unit 16 (and/or camera unit 18) is positioned such that the field of view 52 of the camera head 24 covers the portion of a patient 56 upon which the orthopaedic surgical procedure is to be performed, as shown in FIG. 2.

During the performance of the orthopaedic surgical procedure, the computer 12 of the CAOS system 10 is programmed or otherwise configured to display images of the individual surgical procedure steps which form the orthopaedic surgical procedure being performed. The images may be graphically rendered images or graphically enhanced photographic images. For example, the images may include three dimensional rendered images of the relevant anatomical portions of a patient. The surgeon 50 may interact with the computer 12 to display the images of the various surgical steps in sequential order. In addition, the surgeon may interact with the computer 12 to view previously displayed images of surgical steps, selectively view images, instruct the computer 12 to render the anatomical result of a proposed surgical step or procedure, or perform other surgical related functions. For example, the surgeon may view rendered images of the resulting bone structure of different bone resection procedures. In this way, the CAOS system 10 provides a surgical "walk-through" for the surgeon 50 to follow while performing the orthopaedic surgical procedure.

In some embodiments, the surgeon 50 may also interact with the computer 12 to control various devices of the system 10. For example, the surgeon 50 may interact with the system 10 to control user preferences or settings of the display device 44. Further, the computer 12 may prompt the surgeon 50 for responses. For example, the computer 12 may prompt the surgeon to inquire if the surgeon has completed the current surgical step, if the surgeon would like to view other images, and the like.

The camera unit 16 and the computer 12 also cooperate to provide the surgeon with navigational data during the orthopaedic surgical procedure. That is, the computer 12 determines and displays the location of the relevant bones and the surgical tools 58 based on the data (e.g., images) received from the camera head 24 via the communication link 48. To do so, the computer 12 compares the image data received from each of the cameras 26 and determines the location and orientation of the bones and tools 58 based on the relative location and orientation of the reference arrays 54, 62, 82, 96. The navigational data displayed to the surgeon 50 is continually updated. In this way, the CAOS system 10 provides visual feedback of the locations of relevant bones and surgical tools for the surgeon 50 to monitor while performing the orthopaedic surgical procedure.

Although the reference arrays 54 are illustrated in FIGS. 3-5 and described above as reflective reference array, other types of reference arrays may be used in other embodiments. For example, in some embodiments, the surgical tools 54 may include a magnetic or electromagnetic source such as a permanent magnet. In such embodiments, the location of the surgical tool may be determined based on signals received from a number of magnetic sensors as described in more detail in U.S. patent application Ser. No. 11/323,609, entitled "APPARATUS AND METHOD FOR REGISTERING A BONE OF A PATIENT WITH A COMPUTER ASSISTED ORTHOPAEDIC SURGERY SYSTEM," U.S. patent application Ser. No. 11/323,963, entitled "SYSTEM AND METHOD FOR REGISTERING A BONE OF A PATIENT WITH A COMPUTER ASSISTED ORTHOPAEDIC SURGERY SYSTEM," U.S. patent application Ser. No. 11/323,537, entitled "METHOD FOR DETERMINING A POSITION OF A MAGNETIC SOURCE," and U.S. patent application Ser. No. 11/323,610, entitled "MAGNETIC SENSOR ARRAY," the entirety of each of which is expressly incorporated herein by reference. In such embodiments, the computer assisted orthopaedic surgery system 10 may or may not include the camera unit 14.

Additionally or alternatively, the surgical tools 58 may include a magnetic or electromagnetic sensor. In such embodiments, the location of the surgical tool may be determined based on the signals received by the magnetic and/or electromagnetic sensors as described in more detail in International Patent Application Number PCT/GB2005/000874, entitled "Registration Methods and Apparatus," and in International Patent Application Number PCT/GB2005/000933, entitled "Orthopaedic Operating Systems, Methods, Implants and Instruments", the entirety of each of which is expressly incorporated herein by reference. As such, it should be appreciated that any one or more of the reference arrays 54 may be embodied as a number of reflective elements, a number of magnetic/electromagnetic sensors, and/or a number of magnetic/electromagnetic sources such as permanent magnets. Accordingly, as used herein, the term "reference array" is intended to refer to any number of reflective sensors, magnetic and/or electromagnetic sensors, and/or magnetic and/or electromagnetic sources.

Figure 6:
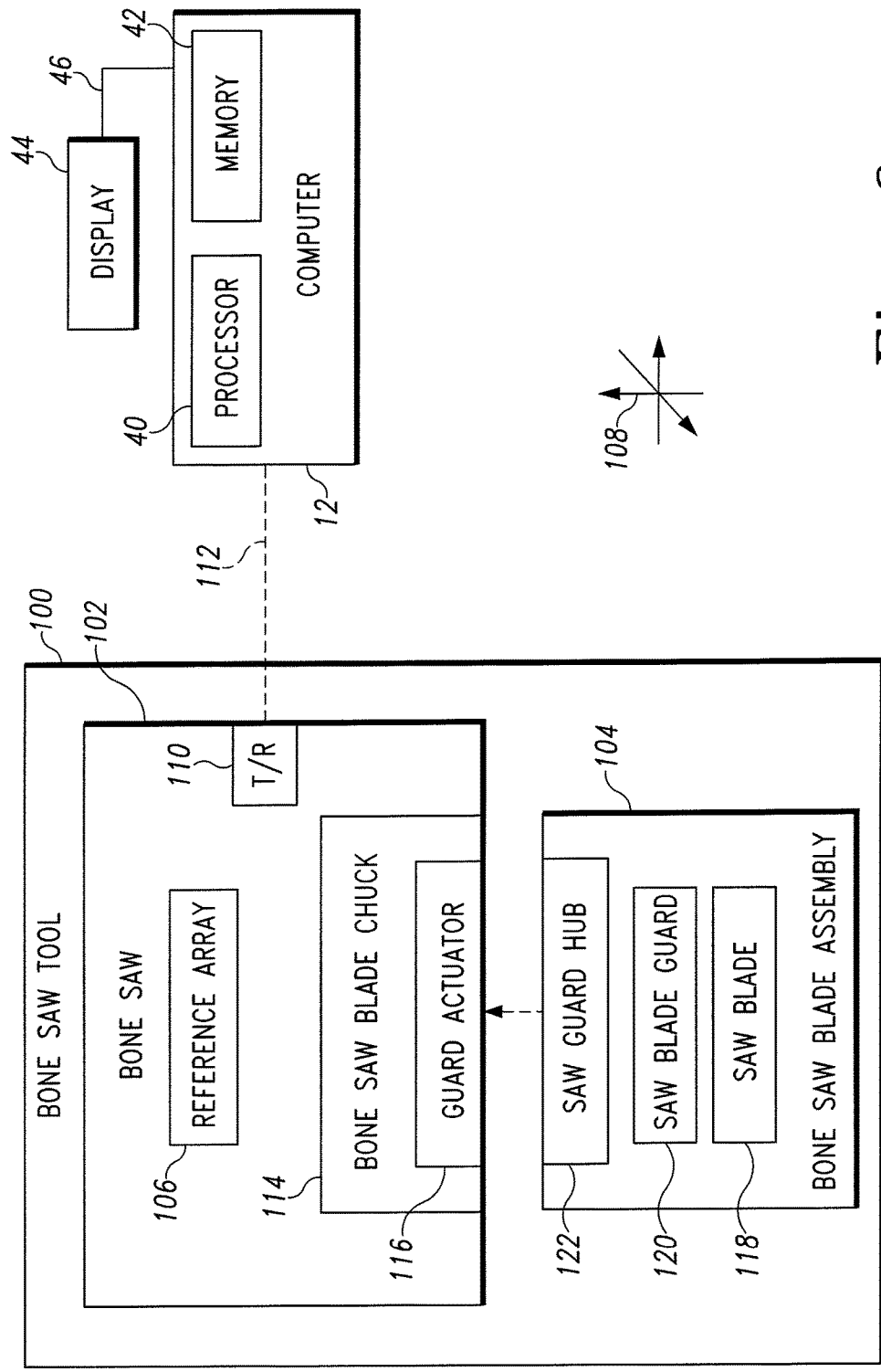
FIG. 6 is a simplified diagram of the computer assisted orthopaedic surgery (CAOS) system of FIG. 2 including a bone saw tool.

Referring now to FIG. 6, in one embodiment, the surgical tool 58 is embodied as a bone saw tool 100. The bone saw tool 100 includes a bone saw 102 and a bone saw blade assembly 104. The bone saw 102 may be similar to a typical bone saw with the modifications and/or functionalities described herein. The bone saw 102 includes a reference array 106. The reference array 106 may be any type of reference array usable by the computer 12 to determine a location of the bone saw tool 100 in a global coordinate system 108. For example, as described above, the reference array 106 may be embodied as any number of reflective sensors, magnetic and/or electromagnetic sensors, and/or magnetic and/or electromagnetic sources. The global coordinate system 108 may be defined by any reference point useable by the computer 12. In some embodiments, the coordinate system 108 is defined by the sensor unit used in cooperation with the reference array 106 to determine the location of the bone saw tool 100. For example, in the embodiment of FIG. 1, the coordinate system 108 may be defined by the camera unit 14 or 18, the computer 12, or another predefine location. Regardless, the computer 12 is configured to determine the location of the bone saw tool 100 in the coordinate system 108 during use as described below in regard to FIG. 20.

The bone saw 102 also includes a receiver or transceiver 110. The bone saw 102 is communicatively coupled to the computer 12 via the receiver 110 and a communication link 112. The communication link 112 may be embodied as any type of communication link capable of facilitating communication between the computer 12 and the bone saw 102. For example, the communication link 112 may be a wired communication link and embodied as any number of wires, cables, or the like. Alternatively, the communication link 112 may be a wireless communication link. In such embodiments, the computer 12 may use any suitable wireless communication technology and protocol to communicate with the bone saw 102 via the communication link 112 such as, for example, a Bluetooth wireless communication protocol, a wireless local area network (WLAN) communication protocol, or the like.

Figure 7:
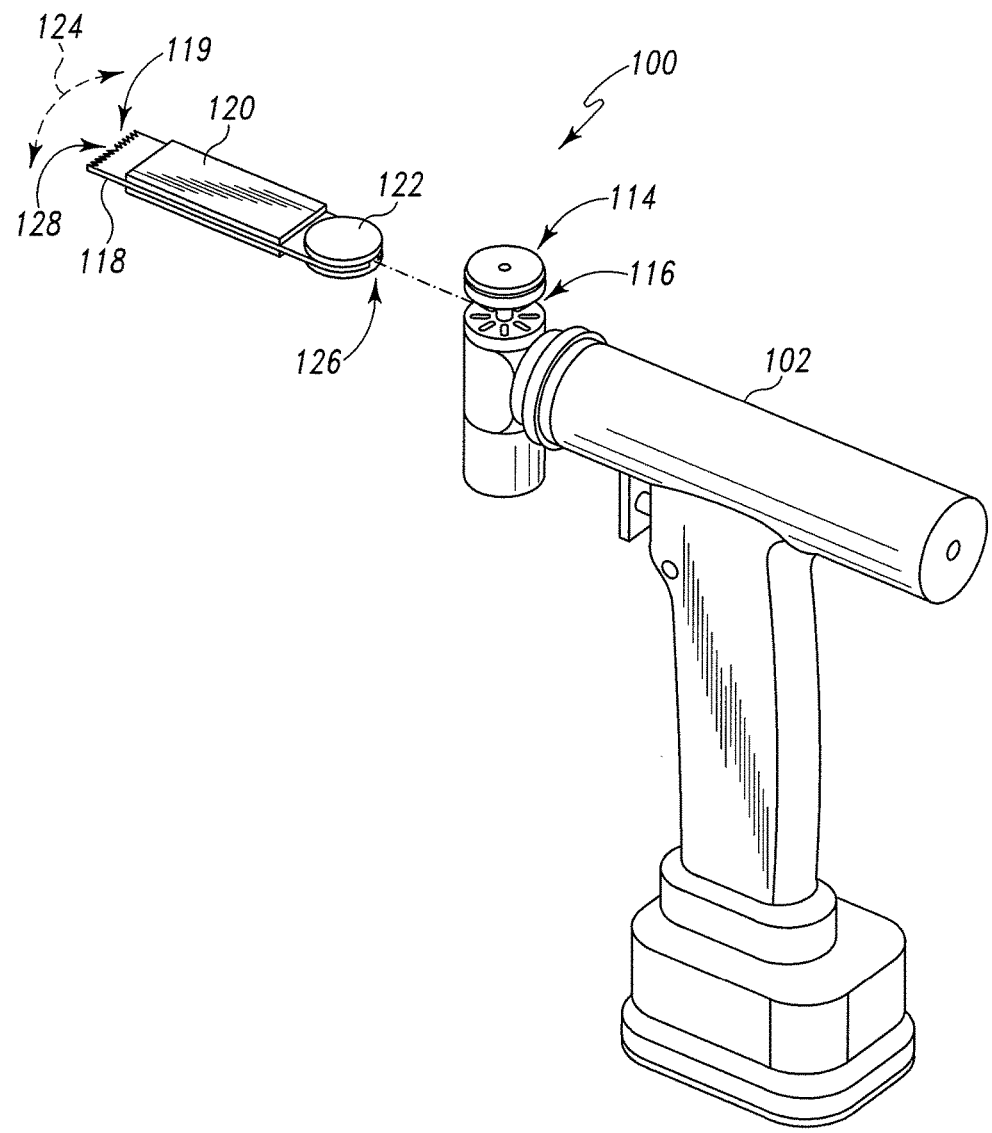
FIG. 7 is a perspective view of one embodiment of the bone saw tool of FIG. 6.

The bone saw 102 also includes a bone saw blade chuck 114. The bone saw blade chuck 114 is configured to receive the bone saw blade assembly 104 as illustrated in FIG. 7. That is, a user may couple the bone saw blade assembly 104 to the bone saw 102 by inserting the bone saw blade assembly 104 into the chuck 114 and operating the chuck 114 to secure the bone saw blade assembly 104 to the bone saw 102. In use, the bone saw blade chuck 114 moves the saw blade assembly 104 in a cutting motion. For example, in some embodiments, as illustrated in FIG. 7, the bone saw blade chuck 114 oscillates the bone saw blade assembly 104 along a cutting arc 124. However, in other embodiments, the bone saw blade assembly 104 may be oscillated or otherwise moved in any direction and along any cutting path depending on the particular application and type of bone saw used.

The bone saw blade assembly includes a bone saw blade 118 and a bone saw blade guard 120. The bone saw blade 118 may be embodied as any type of bone saw blade typically used with bone saws. As illustrated in FIG. 7, the bone saw blade 118 includes a mounting end 126 configured to be received by the bone saw blade chuck 114 of the bone saw 102. The bone saw blade 118 also includes a cutting end 128 having a number of cutting teeth 119. During operation of the bone saw tool 100, the cutting end 128 of the bone saw blade 118 is used to cut the relevant bone of the patient via the oscillating motion generated by the bone saw 102.

The bone saw blade guard 120 is movable with respect to the bone saw blade 118 to reduce the cutting effectiveness of the bone saw blade. That is, the bone saw blade guard 120 is movable between a retracted position and an extended position. When in the bone saw blade guard 120 is in the retracted position, the bone saw blade 118 is able to cut bone when oscillated by the bone saw 102 (e.g., when moved along the arc 124 by the bone saw 102). However, when the bone saw blade guard 120 is moved to the extended position, the bone saw blade 118 is unable to cut bone or otherwise has a reduced cutting effectiveness. It should be appreciated that when in the extended position, the bone saw blade guard 120 reduces the cutting effectiveness of the bone saw blade 118 even if the bone saw 102 continues to oscillate the bone saw blade 118 in a cutting motion (e.g., along the cutting arc 124).

In one particular embodiment, the bone saw blade guard 120 is coupled to the bone saw blade 118 and movable with respect to the bone saw blade 118 to an extended position in a direction substantially parallel with the bone saw blade 118. To facilitate the movement of the bone saw blade 118, the bone saw blade assembly 104 includes one or more saw guard hubs 122. The saw guard hub(s) 122 is operatively coupled to the bone saw blade guard 120 and configured to move the bone saw blade guard 120 between the retracted and extended positions. The saw guard hub(s) 122 is also configured to be coupled to a guard actuator 116 of the bone saw blade chuck when the bone saw blade assembly 104 is coupled thereto. The guard actuator 116 is configured to operate the saw guard hub 122 to thereby cause the saw blade guard 120 to extend or retract with respect to the bone saw 102. The guard actuator 116 may be embodied as any type of prime mover capable of cooperating with the saw guard hub 122 to move the bone saw blade guard 120. For example, the guard actuator 116 may be embodied as a linear actuator, stepper motor, or the like and may include any number and type of gears and/or other linkage to control the operation of the saw guard hub 122.

Referring now to FIGS. 8-11, in one embodiment, the bone saw blade guard 120 is embodied as a first slat 130 positioned on a top side 132 of the bone saw blade 118 and a second slat 134 positioned on a bottom side 136 of the bone saw blade 118. Each of the slats 130, 134 is operatively coupled to a saw guard hub 122 positioned on the corresponding side 132, 136 of the bone saw blade 118. The slats 130, 134 are coupled to the hubs 122 on a back end 140 via a corresponding linkage 142.

Figure 8:
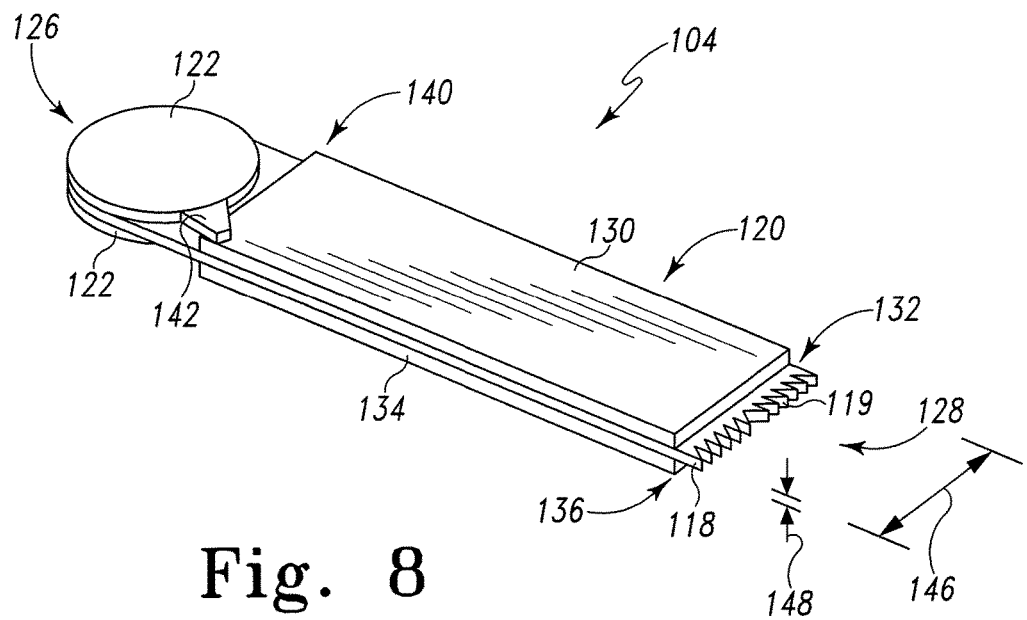
FIG. 8 is a perspective view of one embodiment of a bone saw blade assembly of the bone saw tool of FIG. 6 having a bone saw blade guard in a retracted position.
Figure 9:
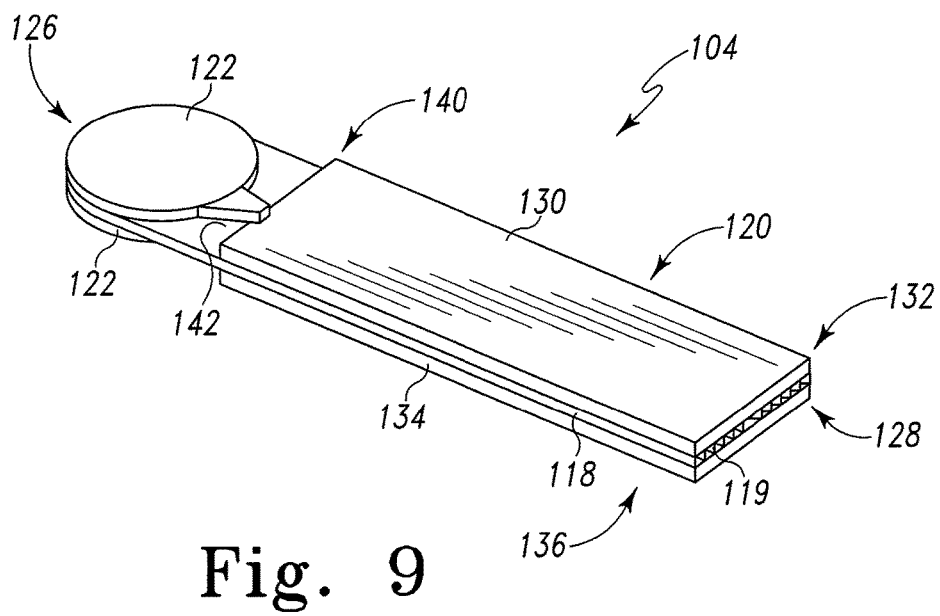
FIG. 9 is a perspective view of the bone saw blade assembly of FIG. 8 having the bone saw blade guard in an extended position.

The slats 130, 134 have dimensions configured to allow the bone saw blade 118 to be oscillated by the bone saw 102 to cut bone when the bone saw guard 120 (i.e., the slats 130, 134) is in the retracted position and reduce the cutting effectiveness of the bone saw blade 118 when in the extended position. Illustratively, as illustrated in FIGS. 8 and 9, the slats 130, 134 have a width 146 and a thickness 148 substantially equal to the width and thickness, respectively, of the bone saw blade 118. However, in other embodiments, the slats 130, 134 may have other dimensions. For example, in some embodiments, the slats 130, 134 may have a width 146 and/or a thickness 148 that is less than or greater than the width and/or thickness of the bone saw blade 118. The slats 130, 134 may be formed from any material that is rigid enough to be moved between the retracted and extended positions and reduce the cutting effectiveness of the bones saw blade 118 when in the extended position. For example, the slats 130, 134 may be formed from a metallic or plastic material. Additionally, in some embodiments, the slats 130, 134 are removable from the bone saw blade assembly 104 such that the slats 130, 134 may be cleaned and/or replaced after each use of the bone saw tool 100.

Figures 10, 11:
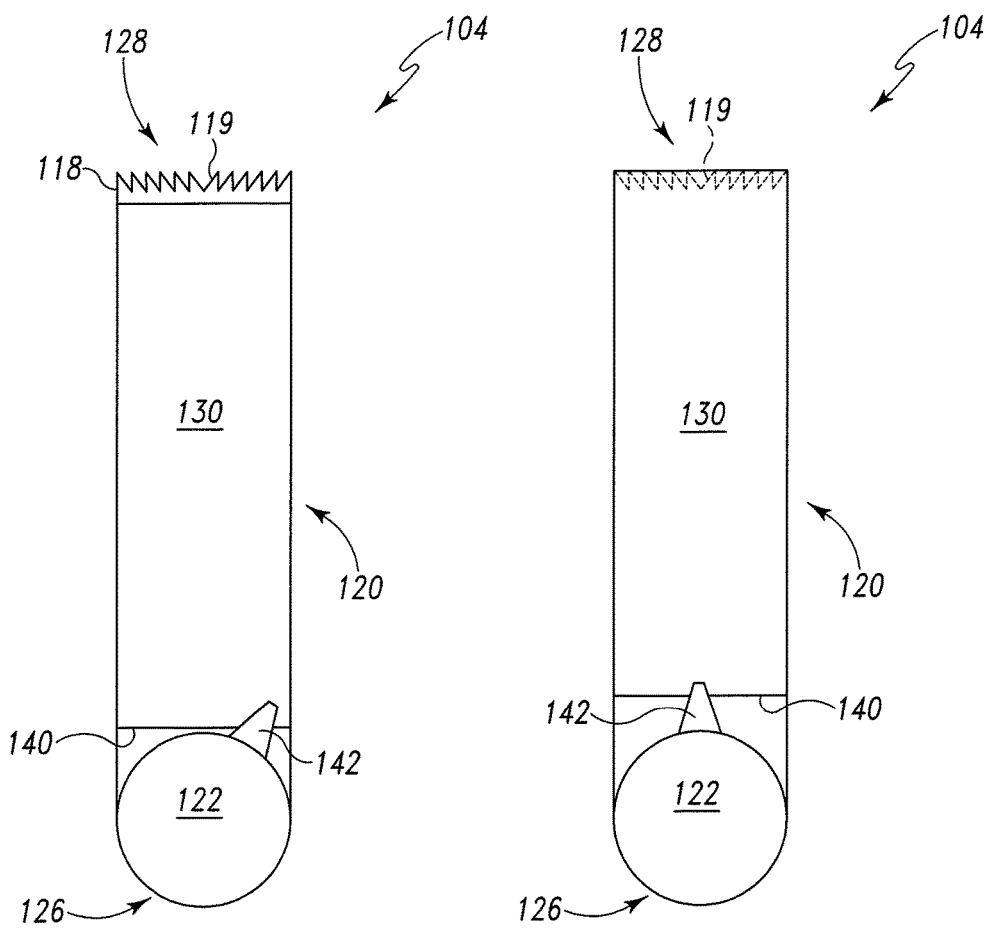
FIG. 10 is a plan view of the bone saw blade assembly of FIG. 8.
FIG. 11 is a plan view of the bone saw blade assembly of FIG. 9.
Figure 16:
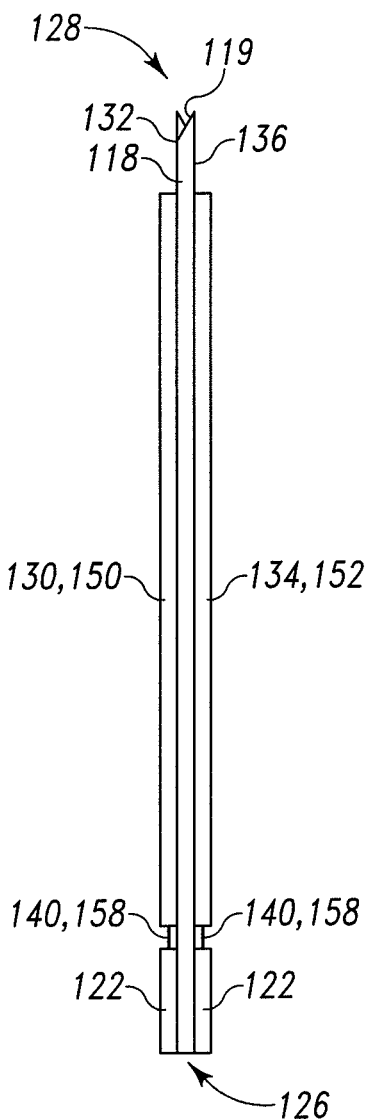
FIG. 16 is a side elevation view of the bone saw assembly of the bone saw tool of FIG. 6 having a bone saw blade guard in a retracted position.

As illustrated in FIGS. 8, 10, and 16, when the slats 130, 134 are in the retracted position, the cutting teeth 119 of the bone saw blade 118 are exposed. As such, the bone saw blade 118 may be used to cut bone when the slats 130, 134 are in the retracted position. As discussed above, the slats 130, 134 may be moved to the extended position via cooperation of the corresponding hub 122 and linkage 142. In the embodiment illustrated in FIGS. 8-11, the linkage 142 is positioned toward a side of the bone saw blade 118 when the slats 130, 134 are in the retracted position. When activated, the hubs 122 move the linkage 142 toward the center of the bone saw blade 118 to cause the slats 130, 134 to be moved to the extended position. However, in other embodiments, other types of linkages and movement methodologies may be used to move the slats 130, 134 between the retracted and extended positions.

Figure 17:
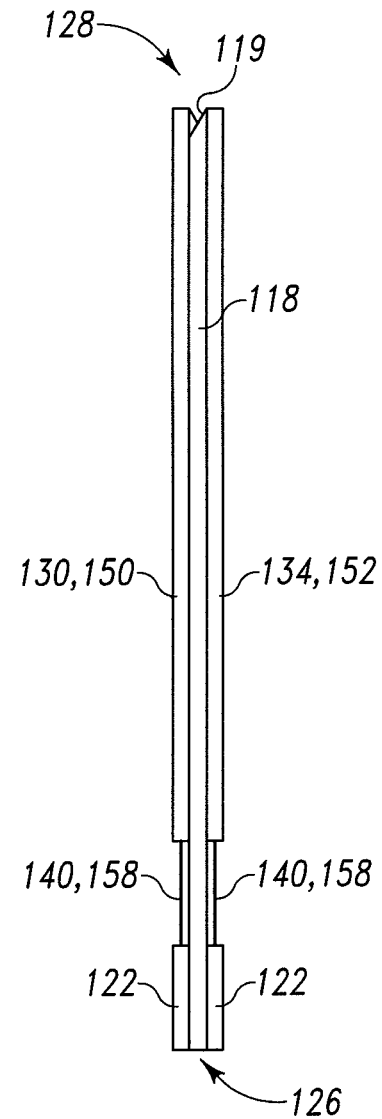
FIG. 17 is a side elevation view of the of the bone saw blade assembly of FIG. 16 having the bone saw blade guard in an extended position.

As illustrated in FIGS. 9, 11, and 17, when the slats 130, 134 are moved to the extended position, the cutting teeth 119 of the bone saw blade 118 are covered by the slats 130, 134. That is, each of the slats 130, 134 covers at least a portion of the cutting teeth 119 on the corresponding side 132, 136 of the bone saw blade 118. For example, in embodiments wherein the width 146 of the slats 132, 136 is equal to or greater than the width of the bone saw blade 118, the slats 130, 134 substantially cover the cutting teeth 119 on the corresponding side 132, 136 of the bone saw blade. Alternatively, in embodiments wherein the width 146 of the slats 132, 136 is less than the width of the bone saw blade 118, the slats 130, 134 may cover only a portion of the cutting teeth 119. Additionally, the slats 130, 134 may or may not extend past the cutting end 128 of the bone saw blade 118 when in the extended position. Regardless, it should be appreciated that when the slats 130, 134 are in the extended position, the slats 130, 134 cover the cutting teeth 119 (or portion thereof) of the bone saw blade 118 as illustrated in FIG. 17 such that the ability of the bone saw blade 118 to cut bone is reduced.

Referring now to FIGS. 12-15, in another embodiment, the bone saw blade guard 120 is embodied as a first number of slats 150 positioned on the top side 132 of the bone saw blade 118 and a second number of slats 152 positioned on a bottom side 136 of the bone saw blade 118. Similar to the slats 130, 134, each of the slats 150, 152 is operatively coupled to a saw guard hub 122 positioned on the corresponding side 132, 136 of the bone saw blade 118. Each of the slats 150 is coupled to a corresponding saw guard hub 122 positioned on the top side 132 of the bone saw blade 118 via a corresponding linkage 154. Similarly, each number of the slats 152 is coupled to a corresponding saw guard hub 122 positioned on the bottom side 134 of the bone saw blade 118 via a corresponding linkage 158.

Figure 12:
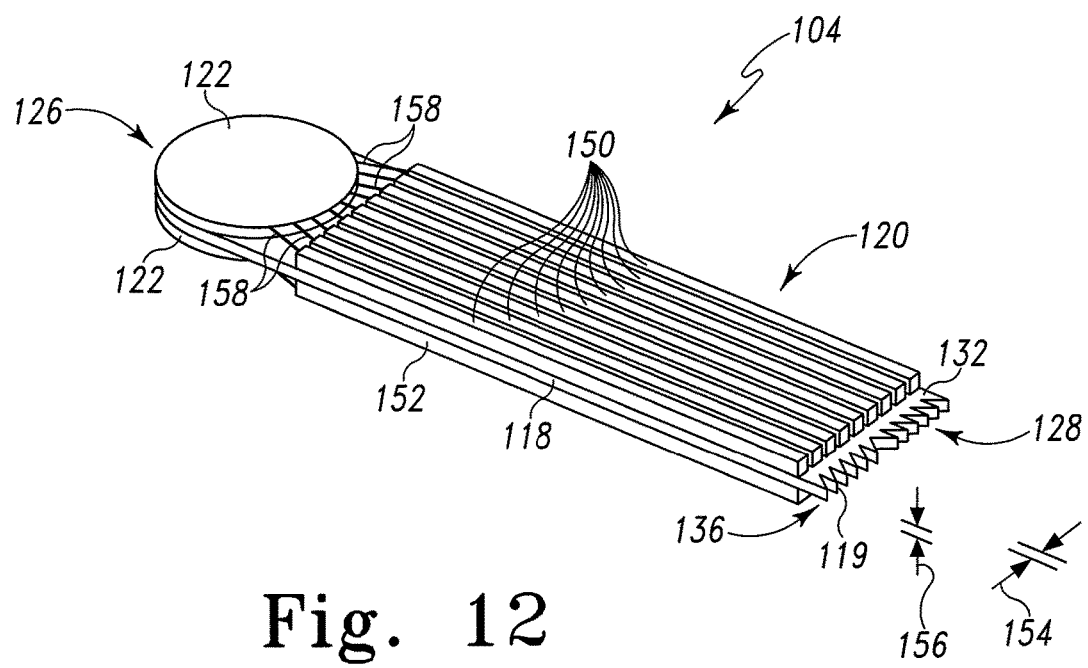
FIG. 12 is a perspective view of another embodiment of the bone saw blade assembly of the bone saw tool of FIG. 6 having a bone saw blade guard in a retracted position.
Figure 14:
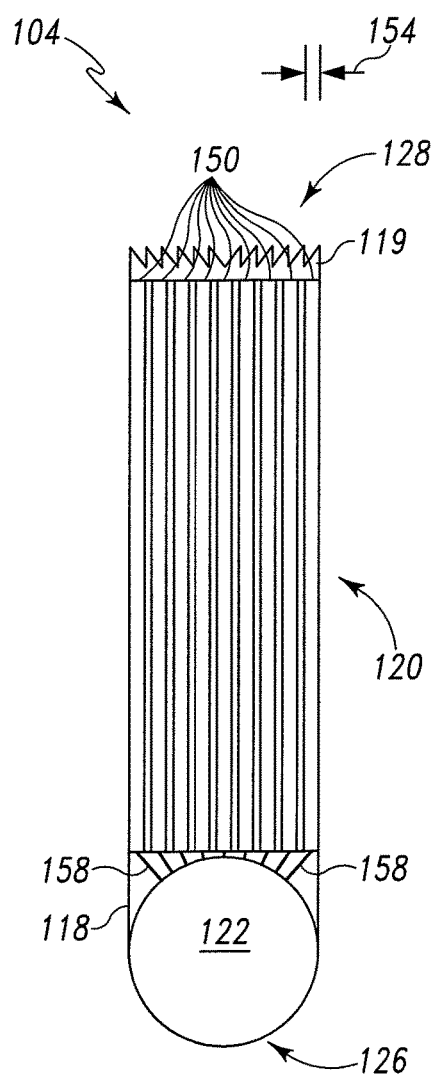
FIG. 14 is a plan view of the bone saw blade assembly of FIG. 12

Each of the slats 150, 152 has dimensions configured to allow the bone saw blade 118 to be properly operated by the bone saw 102 to cut bone when the bone saw guard 120 (i.e., the slats 150, 152) is in the retracted position and reduce the cutting effectiveness of the bone saw blade 118 when in the extended position. Illustratively, as illustrated in FIGS. 12 and 14, each of the slats 150, 152 has a width 154 substantially equal to the width of a single tooth of the number of teeth 119 of the bone saw blade 118. Additionally, as illustrated in FIG. 12, each of the slats 150, 152 may have a thickness 156 substantially equal to or less than the thickness of the bone saw blade 118. However, in other embodiments, each of the slats 150, 152 may have other dimensions. For example, in some embodiments, the slats 150, 152 may have a width 154 less than or greater than the width of a tooth of the number of cutting teeth 119 of the bone saw blade 118.

Similar to the slats 130, 134 illustrated and described above in regard to FIGS. 8-11, the slats 130, 134 may be formed from any material that is rigid enough to be moved between the retracted and extended positions and reduce the cutting effectiveness of the bone saw blade 118 when in the extended position. For example, the slats 150, 152 may be formed from a metallic or plastic material. Additionally, in some embodiments, the slats 150, 152 are removable from the bone saw blade assembly 104 such that the slats 150, 152 may be cleaned and/or replaced after each use of the bone saw tool 100.

Figure 13:
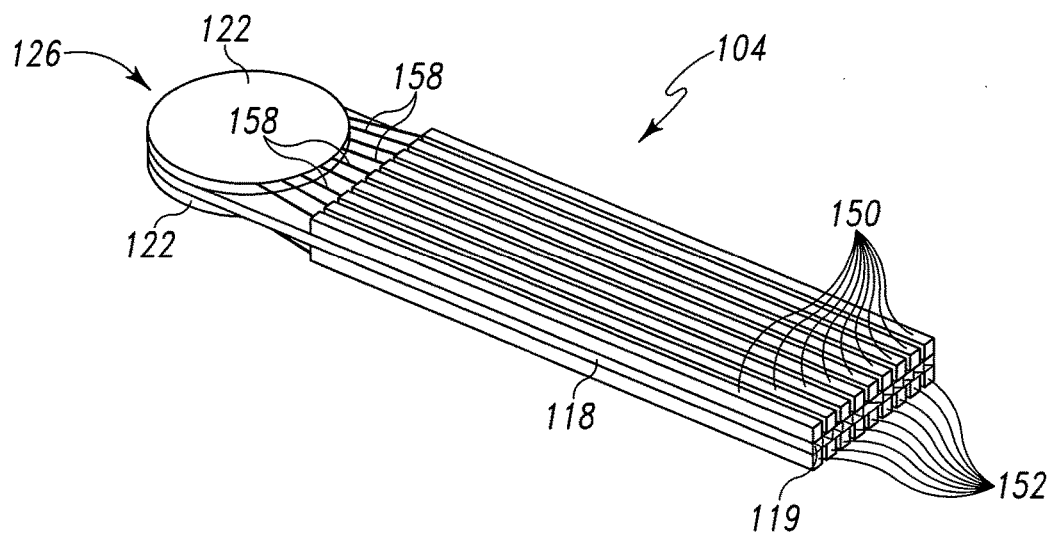
FIG. 13 is a perspective view of the bone saw blade assembly of FIG. 12 having the bone saw blade guard in an extended position.

As illustrated in FIGS. 12, 13, and 16, when the slats 50, 152 are in the retracted position, the cutting teeth 119 of the bone saw blade 118 are exposed. As such, the bone saw blade 118 may be used to cut bone when the slats 150, 152 are in the retracted position. As discussed above, the slats 150, 152 may be moved to the extended position via cooperation of the corresponding hub 122 and linkage 158. In the embodiment illustrated in FIGS. 12-15, the linkage 158 is in a retracted position relative to the hub 122 when the slats 150, 152 are also positioned in the retracted position. When activated, the hubs 122 move the linkage 158 outward with respect to the relative hub 122 to cause the slats 150, 152 to be moved to the extended position. However, in other embodiments, other types of linkages and movement methodologies may be used to move the slats 50, 152 between the retracted and extended positions.

Figure 15:
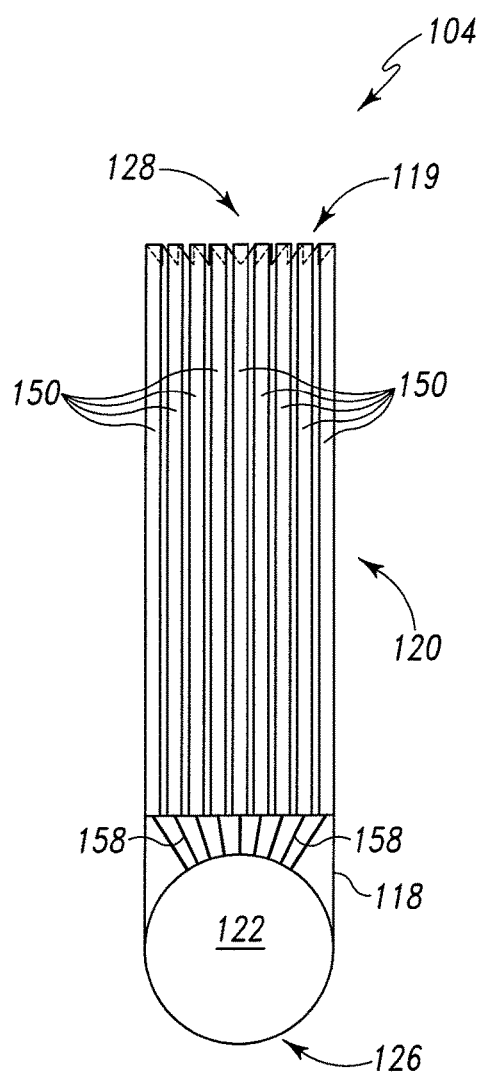
FIG. 15 is a plan view of the bone saw blade assembly of FIG. 13.

As illustrated in FIGS. 13, 15, and 17, when the slats 50, 152 are moved to the extended position, the cutting teeth 119 of the bone saw blade 118 are covered by the slats 150, 152. That is, each of the slats 150, 152 covers at least a portion of one or more of the cutting teeth 119 on the corresponding side 132, 136 of the bone saw blade 118. For example, in embodiments wherein the width 154 of the slats 150, 152 is equal to or greater than the width of a single cutting tooth of the cutting teeth 119, each of the slats 150, 152 completely cover one or more teeth of the cutting teeth 119 on the corresponding side 132, 136 of the bone saw blade. Alternatively, in embodiments wherein the width 154 of the slats 150, 152 is less than the width of a single cutting tooth, the slats 150, 152 may each cover only a portion of a single tooth of the cutting teeth 119 such as, for example, the long edge of each tooth. Additionally, the slats 150, 152 may or may not extend past the cutting end 128 of the bone saw blade 118 when in the extended position. Regardless, it should be appreciated that when the slats 150, 152 are in the extended position, the slats 150, 152 cover the cutting teeth 119 (or portion thereof) of the bone saw blade 118 as illustrate din FIG. 17 such that the ability of the bone saw blade 118 to cut bone is reduced.

Figures 18, 19:
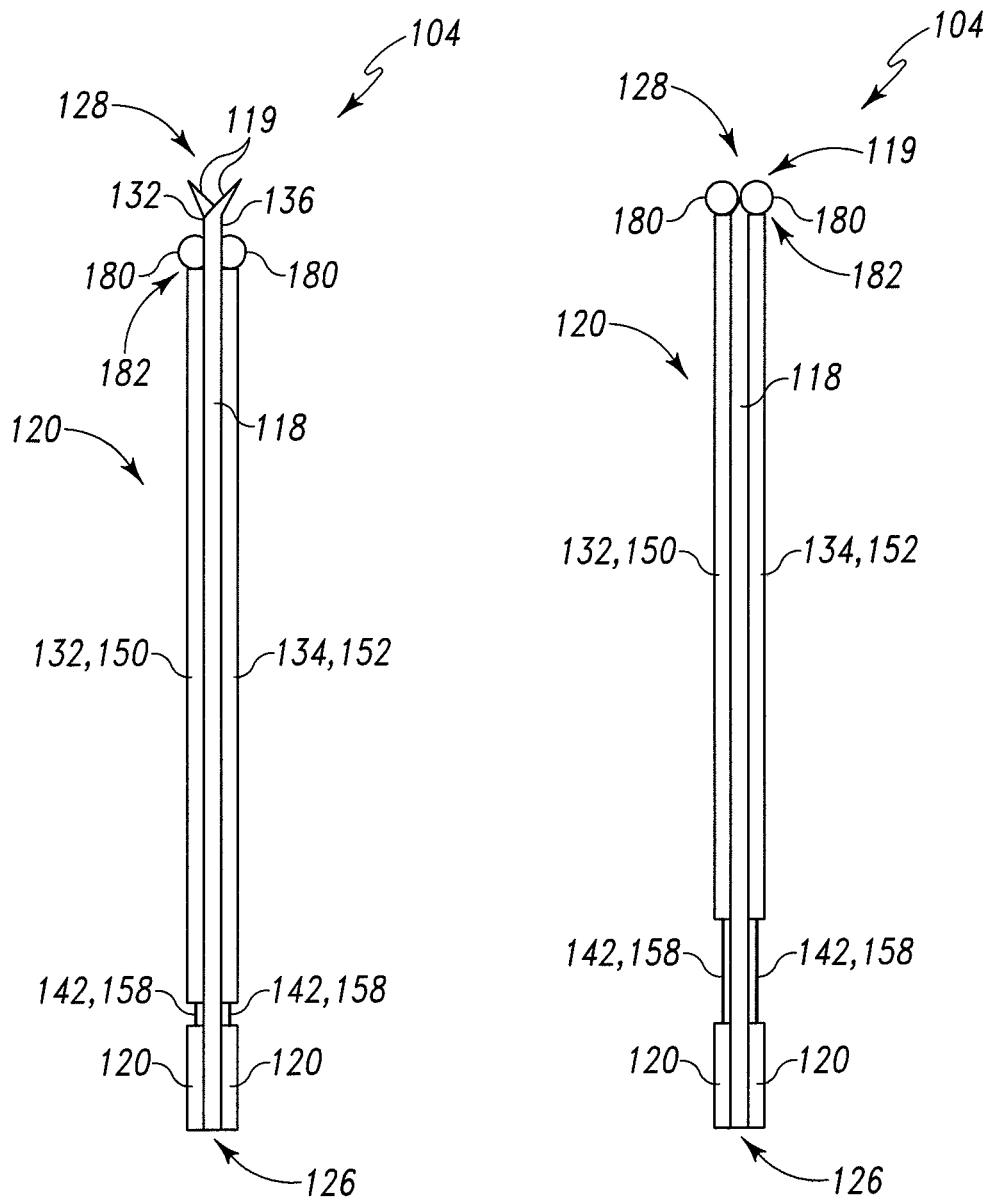
FIG. 18 is a side elevation view of another embodiment of the bone saw assembly of the bone saw tool of FIG. 6 having a bone saw blade guard in a retracted position
FIG. 19 is a side elevation view of the of the bone saw blade assembly of FIG. 18 having the bone saw blade guard in an extended position.

Referring now to FIGS. 18 and 19, the bone saw blade guard 120 may include one or more cutting teeth guards 180 in embodiments wherein the cutting teeth 119 of the bone saw blade 118 are formed such that a portion of each tooth 119 extends upwardly past the top side 132 of the bone saw blade 118 or downwardly past the bottom side 126 of the bone saw blade 118. In such embodiments, the cutting teeth guards 180 are positioned at a distal end 182 of the bone saw blade guard 120 (e.g., at a distal end of each slat 132, 134, 150, 152). The cutting teeth guards 180 may be embodied as any type guard capable of reducing the ability of the tip of the cutting teeth 119 to cut bone when the saw blade guard 120 is in the extended position. For example, as illustrated in FIGS. 18 and 19, the cutting teeth guards 180 may be embodied as a number of spherical bumpers coupled to the distal end 182 of each slat 132, 134, 150, 152. Each of the cutting teeth guards 180 has a diameter greater than the distance from the relevant surface 132, 136 of the bone saw blade 118 and the tip of the corresponding cutting tooth of the number of cutting teeth 119. As such, when the bone saw blade guard 120 is moved to the extended position, the cutting teeth guards 180 reduces the likelihood that the tip of the corresponding cutting tooth inadvertently cuts bone or tissue. It should be appreciated, however, that in other embodiments, the cutting tooth guards 180 may be embodied as other types of guard and/or have other dimensions and shapes configured to restrict the cutting effectiveness of the tip portions of the cutting teeth 119 when the bone saw blade guard 120 is in the extended position.

Referring now to FIGS. 20-22, in another embodiment, the bone saw blade guard 120 is embodied as a number of slats 200. Each of the slats 200 is positioned in a corresponding slot 202 defined in the bone saw blade 118 such that each of the slats 200 is coplanar with the bone saw blade 118. The slots 202 extend longitudinally and are defined between each elongated bone saw tooth 204 of the bone saw blade 118. Each of the slats 202 are configured to slide within the corresponding slot with respect to the cutting blade 118 as discussed in more detail below.

Similar to the slats 130, 134, 150, each of the slats 200 is operatively coupled to a saw guard hub 206 positioned on the top side 132 or bottom side 134 of the bone saw blade 118. Each of the slats 200 is coupled to the saw guard hub 206 via a corresponding linkage 208. To increase the rigidity of the bone saw blade 118, the bone saw blade assembly 120 may include a band or tie 210 to couple the bone saw blade teeth 204 and the slats 200 together. In one embodiment, as illustrated in FIGS. 20 and 22, each of the bone saw teeth 204 includes an aperture 212 defined in a side 214 of the tooth 204. Similarly, each of the slats 200 includes a corresponding aperture 216 defined in a side of the slat 200. The apertures 216 of the slats 200 are embodied as slots or are otherwise elongated relative to the apertures 214 defined in the bone saw teeth 204. Such a configuration allows the slats 200 to translate relative to the bone saw blade 118 while remaining coupled to the bone saw blade 118 (via the teeth 204). In some embodiments, the band or ties 210 may also wrap around the bone saw blade 118 to provide additional support to the blade 118.

Each of the slats 200 has dimensions configured to allow the bone saw blade 118 to be properly operated by the bone saw 102 to cut bone when the bone saw guard 120 (i.e., the slats 200) is in the retracted position and reduce the cutting effectiveness of the bone saw blade 118 when in the extended position. Illustratively, each of the slats 200 has a width substantially equal to the width of one of the saw blade teeth 204. Additionally, each of the slats 200 may have a thickness substantially equal to the thickness of the bone saw blade 118. However, in other embodiments, each of the slats 200 may have other dimensions. For example, in some embodiments, the slats 200 may have a width less than or greater than the width of one of the saw blade teeth 204.

The slats 200 may be formed from any material that is rigid enough to be moved between the retracted and extended positions and reduce the cutting effectiveness of the bone saw blade 118 when in the extended position. For example, the slats 200 may be formed from a metallic or plastic material. Additionally, in some embodiments, the slats 200 are removable from the bone saw blade assembly 104 such that the slats 200 may be cleaned and/or replaced after each use of the bone saw tool 100.

As illustrated in FIG. 20, when the slats 200 are in the retracted position, the cutting teeth 204 of the bone saw blade 118 are exposed. As such, the bone saw blade 118 may be used to cut bone when the slats 200 are in the retracted position. As discussed above, the slats 200 may be moved to the extended position via cooperation of the corresponding hub 206 and linkage 208. The linkage 208 is in a retracted position relative to the hub 206 when the slats 200 are also positioned in the retracted position. When activated, the hubs 206 move the linkage 208 outward to cause the slats 200 to be moved to the extended position. However, in other embodiments, other types of linkages and movement methodologies may be used to move the slats 200 between the retracted and extended positions. It should be appreciated that because the slats 200 are positioned between and coplanar with the cutting teeth 204 of the bone saw blade 118 the likelihood of jamming of the bone saw tool 100 may be reduced. Additionally, in some embodiments, the thickness of the slats 200 is designed to be less than the thickness of each cutting teeth 204 to further reduce the likelihood of jamming.

As illustrated in FIG. 21, when the slats 200 are moved to the extended position, the slats 200 extend outwardly relative to the bone saw blade 118 a distance greater than the cutting teeth 204. Because the slats 200 extend past the ends of the cutting teeth 204, the cutting teeth 204 are restricted from cutting. As such, when the slats 200 are in the extended position, the ability of the bone saw blade 118 to cut bone is reduced or otherwise negated.

Referring now to FIGS. 23-26, in another embodiment, the bone saw blade guard 120 is embodied as a fork 350 including a number of slats 300. The slats 300 are similar to the slats 200 described above in regard to FIGS. 20-22. For example, each of the slats 300 is positioned in a corresponding slot 302 defined in the bone saw blade 118 such that each of the slats 300 is coplanar with the bone saw blade 118. The slots 302 extend longitudinally and are defined between each bone saw cutting tooth 304 of the bone saw blade 118. The cutting teeth 304 are elongated relative to the cutting teeth 119, but shorter than the elongated cutting teeth 204 described above in regard to FIGS. 20-22. That is, the slots 302 extend into the blade 118 a relatively short distance. Because the length of each individual cutting tooth 304 is reduced, the overall rigidity of the bone saw blade 118 may be maintained. The fork 350 also includes a cross-member 306 coupled to each of the slats 300. An elongated push rod 308 is coupled to the cross-member 306. In some embodiments, the slats 300, cross-member 306, and push rod 308 are separate pieces secured or coupled together. However, in other embodiments, the slats 300, cross-member 306, and push rod 308 may be integral with each other.

Figure 23:
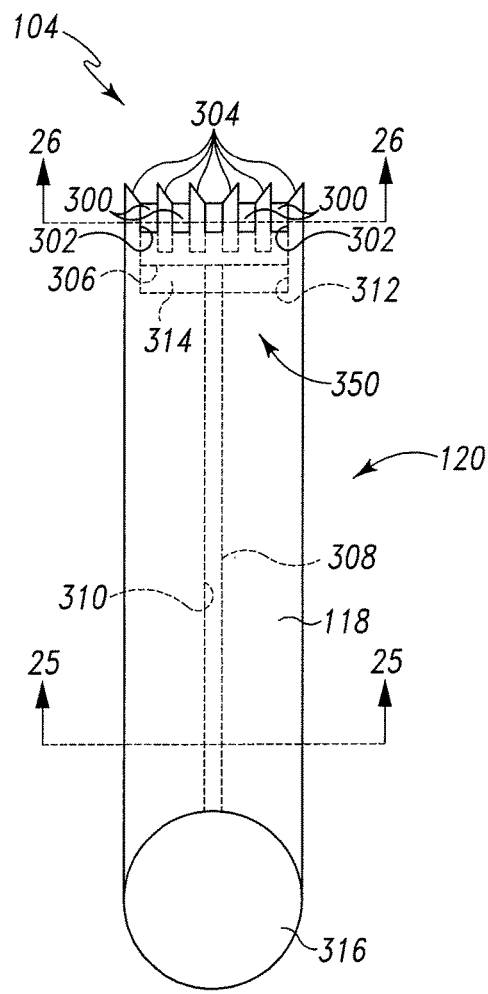
FIG. 23 is a plan view of another embodiment of the bone saw blade assembly of the bone saw tool of FIG. 6 having a bone saw blade guard in a retracted position.
Figure 24:
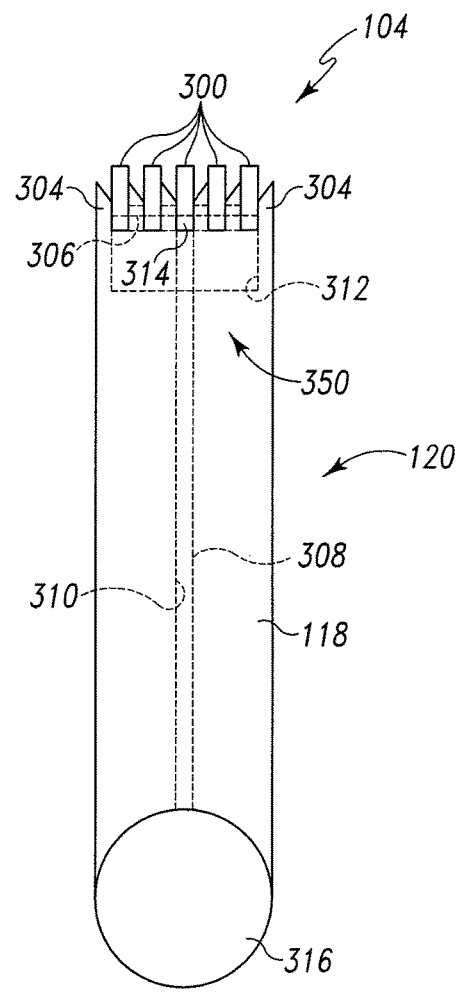
FIG. 24 is a plan view of the bone saw blade assembly of FIG. 23 having the bone saw blade guard in an extended position.
Figure 25:
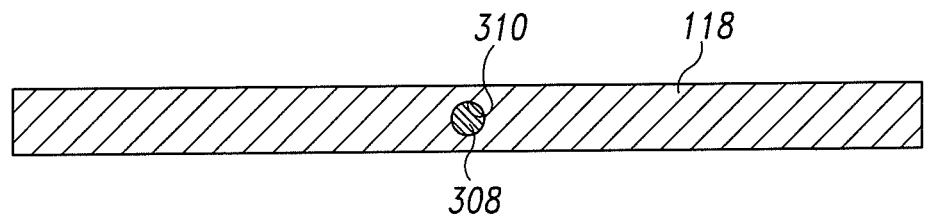
FIG. 25 is a cross-sectional view of the bone saw blade assembly of FIG. 23 taken generally along the lines 25-25.

The push rod 308 of the fork 350 is operatively coupled to a saw guard hub 316, which may be positioned on the top side 132 or bottom side 134 of the bone saw blade 118. The hub 316 is operable to extend the push rod 308, which resultantly moves each of the slots 300 to an extended position as illustrated in FIG. 24 and discussed in more detail below. As illustrated in FIG. 23-25, the push rod 308 is positioned in a longitudinal passageway 310 defined in the bone saw blade 118. During use, the push rod 308 moves within the passageway 310 as discussed in more detail below. Similar to the push rod 308, the cross-member 306 is positioned in an inner cavity 312 defined in the bone saw blade 118 toward the cutting end 314 of the blade 118. In the retracted position as shown in FIG. 23, a portion of each slat 300 is also received in the inner cavity 312. Again, similar to the push rod 308, the cross-member 306 and slats 300 move in the inner cavity 312 during use. In some embodiments, the fork 350 may include a shield 314 coupled to the cross-member 306 and/or push rod 308. The shield 314 is also positioned in the inner cavity 312 and is used to cover any openings defined between the cutting teeth 304 when the bone saw blade guard 120 is in the extended position to restrict the lodging of foreign objects therein. Alternatively, in other embodiments, the cross-member 306 of the fork 350 may be formed to have a width such that the cross-member 306 covers any openings defined between the cutting teeth 304 when the bone saw blade guard 120 is in the extended position.

Figure 26:
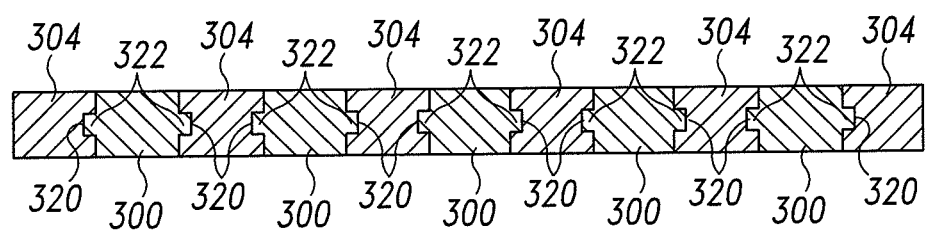
FIG. 26 is a cross-sectional view of the bone saw blade assembly of FIG. 23 taken generally along the lines 26-26.

Additionally, in some embodiments as illustrated in FIG. 26, the cutting teeth 304 include longitudinal slots 320 defined in the sidewalls of each cutting tooth 304. In such embodiments, the slats 300 include a corresponding rail 322 protruding from each sidewall of each slat 300. The rails 322 are received in the slots 320 and are configured to slide or translate therein during operation. Because slots 300 and cutting teeth 304 are mated together in this way, the overall rigidity of the bone saw blade 118 may be improved.

Each of the slats 300 has dimensions configured to allow the bone saw blade 118 to be properly operated by the bone saw 102 to cut bone when the bone saw guard 120 (i.e., the slats 300) is in the retracted position and reduce the cutting effectiveness of the bone saw blade 118 when in the extended position. Illustratively, each of the slats 300 has a width substantially equal to the width of one of the saw blade teeth 304. Additionally, each of the slats 300 may have a thickness substantially equal to the thickness of the bone saw blade 118. However, in other embodiments, each of the slats 300 may have other dimensions. For example, in some embodiments, the slats 300 may have a width less than or greater than the width of one of the saw blade teeth 304.

The slats 300 may be formed from any material that is rigid enough to be moved between the retracted and extended positions and reduce the cutting effectiveness of the bone saw blade 118 when in the extended position. For example, the slats 300 may be formed from a metallic or plastic material. Additionally, in some embodiments, the slats 300 are removable from the bone saw blade assembly 104 such that the slats 300 may be cleaned and/or replaced after each use of the bone saw tool 100.

As illustrated in FIG. 23, when the slats 300 are in the retracted position, the cutting teeth 304 of the bone saw blade 118 are exposed. As such, the bone saw blade 118 may be used to cut bone when the slats 300 are in the retracted position. As discussed above, the slats 300 may be moved to the extended position via cooperation of the corresponding hub 316 and push rod 308. The push rod 308 is in a retracted position relative to the hub 316 when the slats 300 are also positioned in the retracted position. When activated, the hub 316 moves the push rod 308 outward to cause the slats 300 to be moved to the extended position. However, in other embodiments, other types of linkages and movement methodologies may be used to move the slats 300 between the retracted and extended positions. It should be appreciated that because the slats 300 are positioned between and coplanar with the cutting teeth 304 of the bone saw blade 118 the likelihood of jamming of the bone saw tool 100 may be reduced. Additionally, in some embodiments, the thickness of the slats 300 is designed to be less than the thickness of each cutting teeth 304 to further reduce the likelihood of jamming.

As illustrated in FIG. 24, when the slats 300 are moved to the extended position, the slats 300 extend outwardly relative to the bone saw blade 118 a distance greater than the cutting teeth 304. Because the slats 300 extend past the ends of the cutting teeth 304, the cutting teeth 304 are restricted from cutting. As such, when the slats 300 are in the extended position, the ability of the bone saw blade 118 to cut bone is reduced or otherwise negated.

Figure 27:
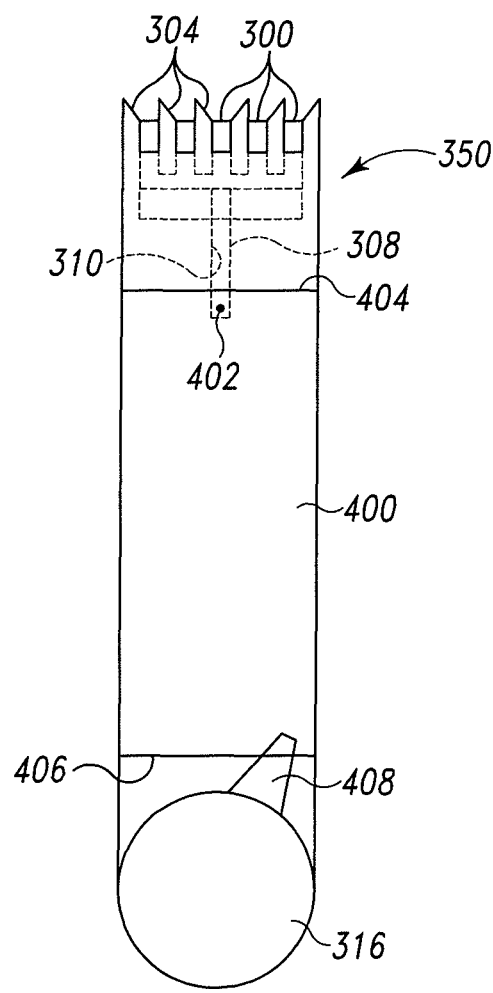
FIG. 27 is a plan view of another embodiment of the bone saw blade assembly of the bone saw tool of FIG. 6 having a bone saw blade guard in a retracted position.
Figure 28:
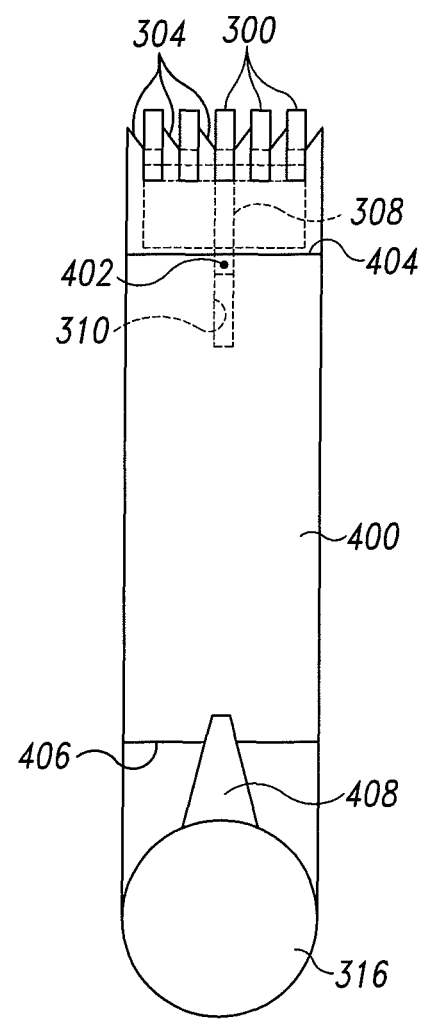
FIG. 28 is a plan view of the bone saw blade assembly of FIG. 27 having the bone saw blade guard in an extended position.

Referring now to FIGS. 27 and 28, the bone saw blade assembly 104 may include a cover, sleeve, or outer slat 400 positioned on a top or bottom side of the bone saw blade 118 and coupled to the push rod 308. In such embodiments, the length of the push rod 308 and corresponding inner passage 310 is reduced. The outer slat 400 is coupled to the push rod 308 via a pin or other securing device 402 on an end 404 and to the hub 316 on an opposite end 406 via a linkage 408. In use, the hub 316 is configured to control or otherwise move the linkage 408 to cause the outer slat 400 to extend or retract relative to the hub 316. When the outer slat 400 is extended, as shown in FIG. 28, the push rod 308 translates or slides in the passageway 310 to cause the slats 300 to cause the slats 300 to be moved to the extended position in the manner described above in regard to FIGS. 23-24.

Figure 29:
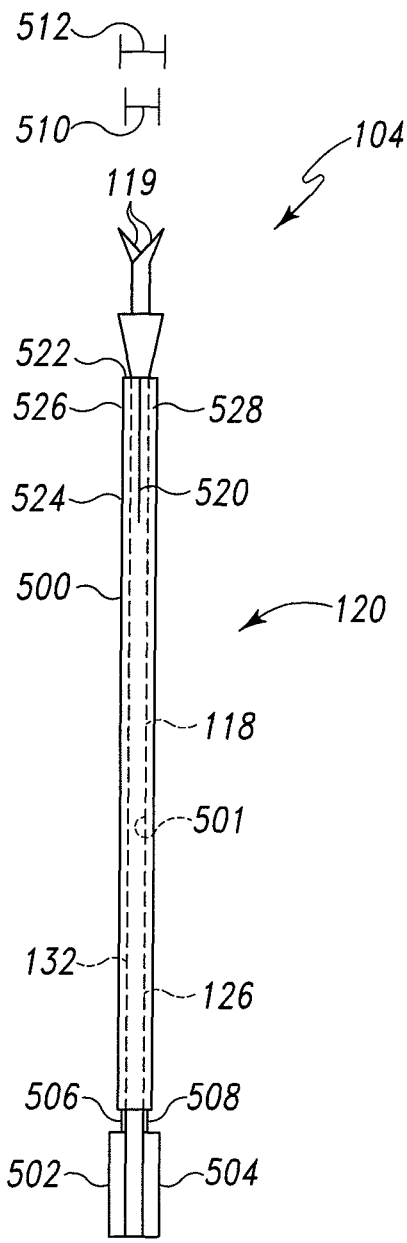
FIG. 29 is a side elevation view of another embodiment of the bone saw assembly of the bone saw tool of FIG. 6 having a bone saw blade guard in a retracted position
Figure 30:
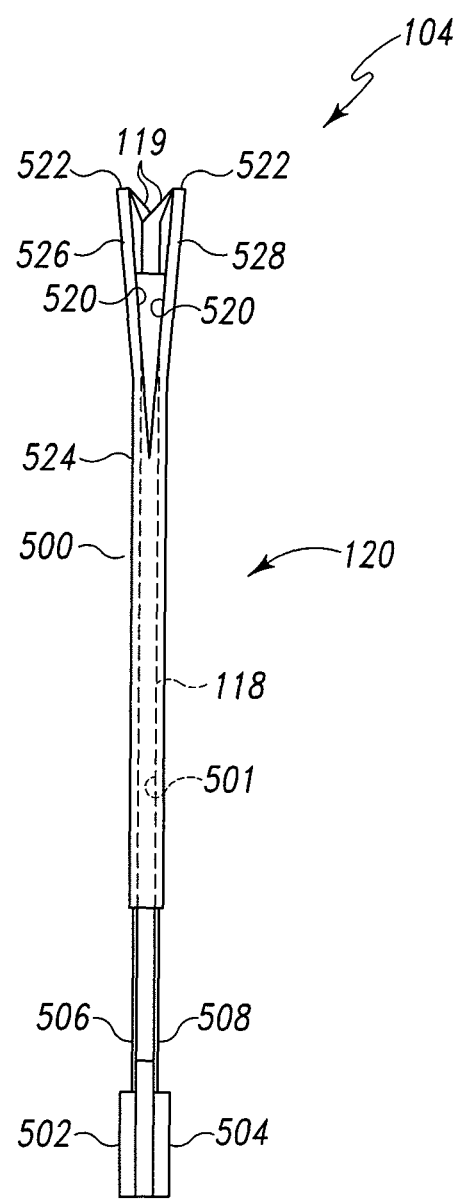
FIG. 30 is a side elevation view of the of the bone saw blade assembly of FIG. 29 having the bone saw blade guard in an extended position.

Referring now to FIGS. 29 and 30, the bone saw blade guard 120 may be embodied as a sleeve 500 in embodiments wherein the cutting teeth 119 of the bone saw blade 118 are formed such that a portion of each tooth 119 extends upwardly past the top side 132 of the bone saw blade 118 or downwardly past the bottom side 126 of the bone saw blade 118. The sleeve 500 includes an inner chamber 501 in which a portion of the bone saw blade 118 is positioned. The sleeve 500 is coupled to one or more hubs 502, 504 via linkages 506, 508, respectively. The sleeve 500 has a thickness 510 that is less than the distance 512 between the tips of the cutting teeth 119 to thereby reduce the likelihood of jamming of the bone saw tool 100. The sleeve includes a slit 520 defined at an end 522 positioned toward the cutting teeth 119. The slit 520 is defined in each sidewall 524 of the sleeve and defines an upper cover portion 526 and a lower cover portion 528 of the sleeve 500.

During use, the hub(s) 502, 504 may be activated to cause the sleeve 500 to retract or extend relative to the hubs 502, 504 via the linkages 506, 508. When the bone saw blade guard 120 is in retracted position, the bone saw blade 118 extends out of the sleeve 500 and the upper and lower cover portions 526, 528 of the sleeve are closed toward each other as shown in FIG. 29. However, when the bone saw blade guard 120 is in the extended position, the sleeve 500 is moved forwarded such that the upper and lower cover portions 526, 528 flex outwardly relative to each over and extend over the cutting teeth 119 of the bone saw blade 118 as shown in FIG. 30. The sleeve 500 may be formed such that the end 522 of the sleeve 500 extends up to or past the cutting teeth 119. As such, when the bone saw blade guard 120 is moved to the extended position, the sleeve 500 reduces the cutting effectiveness of the bone saw blade 118.

Figure 31:
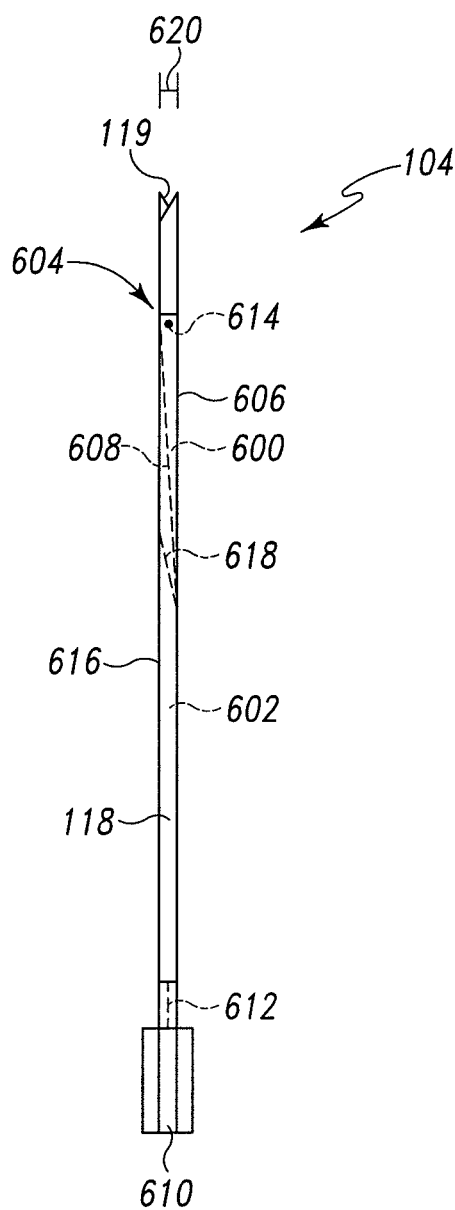
FIG. 31 is a side elevation view of another embodiment of the bone saw assembly of the bone saw tool of FIG. 6 having a bone saw blade guard in a retracted position
Figure 32:
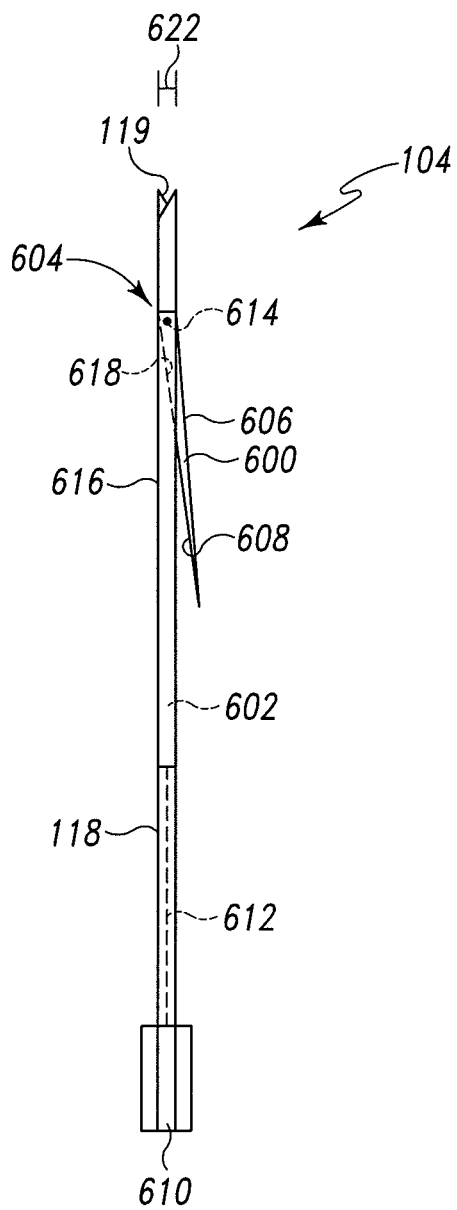
FIG. 32 is a side elevation view of the of the bone saw blade assembly of FIG. 30 having the bone saw blade guard in an extended position.
Figure 33:
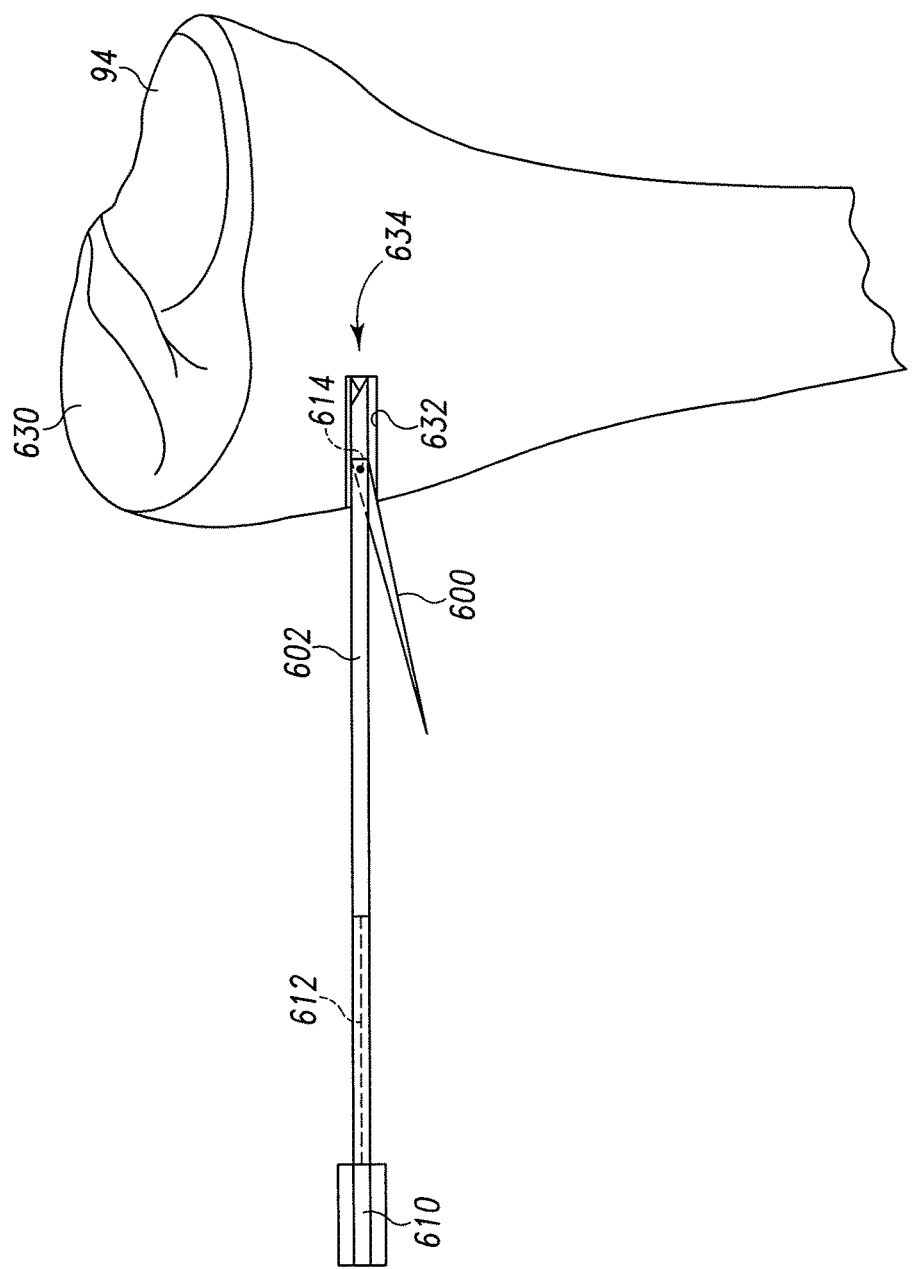
FIG. 33 is a side elevation view of the bone saw blade assembly of FIG. 30 during a bone resectioning procedure.

In addition to or alternatively to the bone saw guard 120, other devices and methodologies may be used to control the cutting effectiveness of the bone saw blade 118. For example, as illustrated in FIGS. 31-33, the bone saw blade assembly 120 may include a first wedge 600 and a second wedge 602 defined within an aperture of the bone saw blade 118 such that the wedges 600, 602 are positioned in the volume defined by the bone saw blade 118. The first wedge 600 is pivotably secured to the bone saw blade 118 at an end 604 toward the cutting teeth 119 via a hinge 614. Illustratively, the first wedge 600 includes a substantially planar bottom side 606 and an angled top side 608.

The second wedge 602 is operatively coupled to a saw guard hub 610 via a linkage 612. The wedge 602 includes a substantially planar top side 616 and an angled bottom side 618. The wedge 602 is positioned such that the angled side 618 of the wedge 602 confronts or abuts the angled side 608 of the wedge 600.

The wedge 602 may be retracted or extended by the hub 610. In the retracted position, as shown in FIG. 31, the wedges 600, 602 do not protrude beyond the sides of the bone saw blade 118. As such, the bone saw blade assembly 104 has a thickness 620 equal to the thickness of the bone saw blade 118. However, when the wedge 602 is positioned in the extended position, the wedge 602 slides forward causing the wedge 600 to be pushed outwardly with respect to the bone saw blade 118. As such, in the extended position, the bone saw blade assembly 104 has a thickness 622 defined by the bone saw blade 118 and the wedge 600 that is greater than the thickness 620. That is, the thickness of the assembly 104 is controllable via positioning of the wedge 602.

In use, as illustrated in FIG. 33, the thickness of the bone saw blade assembly 104 may be controlled to thereby control the cutting depth of the bone saw blade 118 into a bone 630 of a patient. To do so, the saw guard hub 610 causes the wedge 602 to extend to a desired distance, which selectively changes the thickness of the bone saw blade assembly 104. As such, when the desired cutting depth of the blade 118 is achieved, the blade 118 and/or wedge 600 contact a side 632 of the bone cut 634 thereby restricting the blade 118 from cutting deeper or sideways. Additionally, in some embodiments, the bone saw blade assembly 104 will become fixed in the bone cut 634 when the wedge 602 is in the extended position. The bone saw blade assembly 104 may be withdrawn from the bone cut 634 by retracting the wedge 602 and/or removing power from the bone saw 102.

Figure 34:
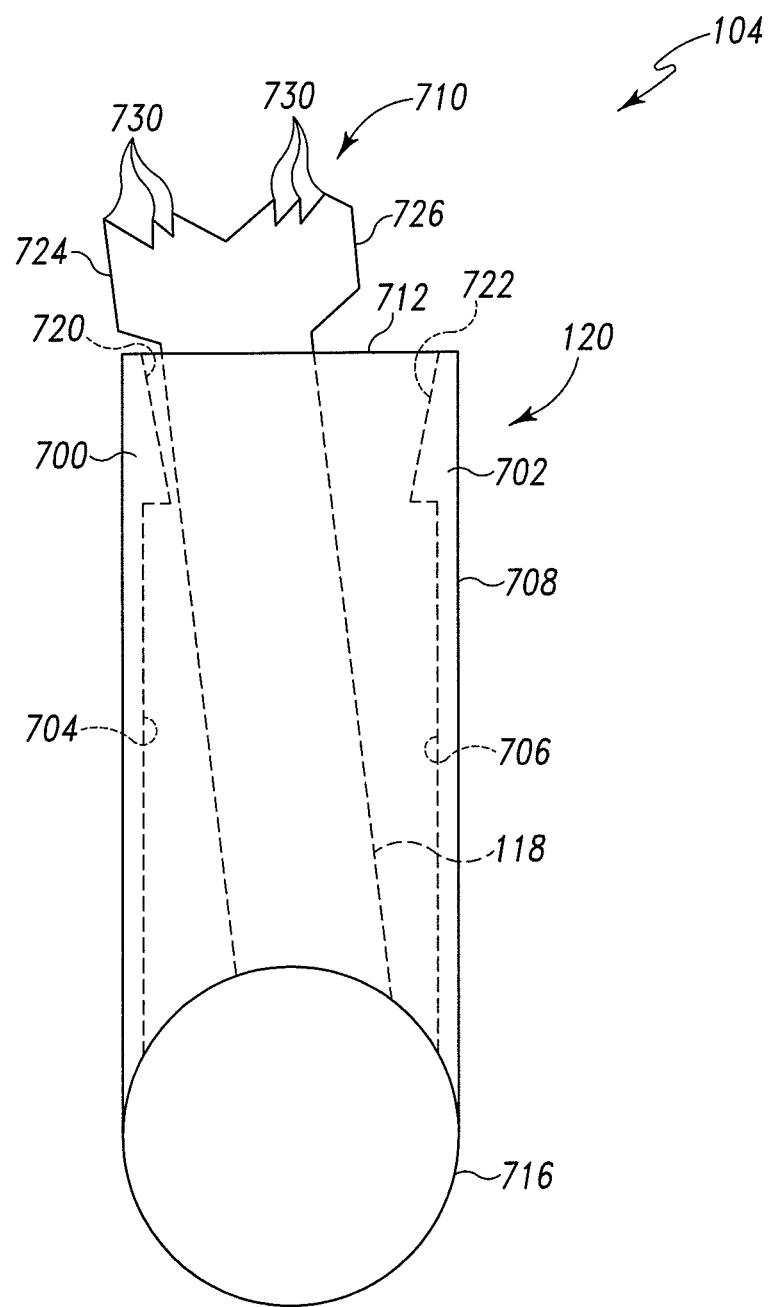
FIG. 34 is a top plan view of another embodiment of the bone saw assembly of the bone saw tool of FIG. 6 having a bone saw blade guard in a retracted position
Figure 35:
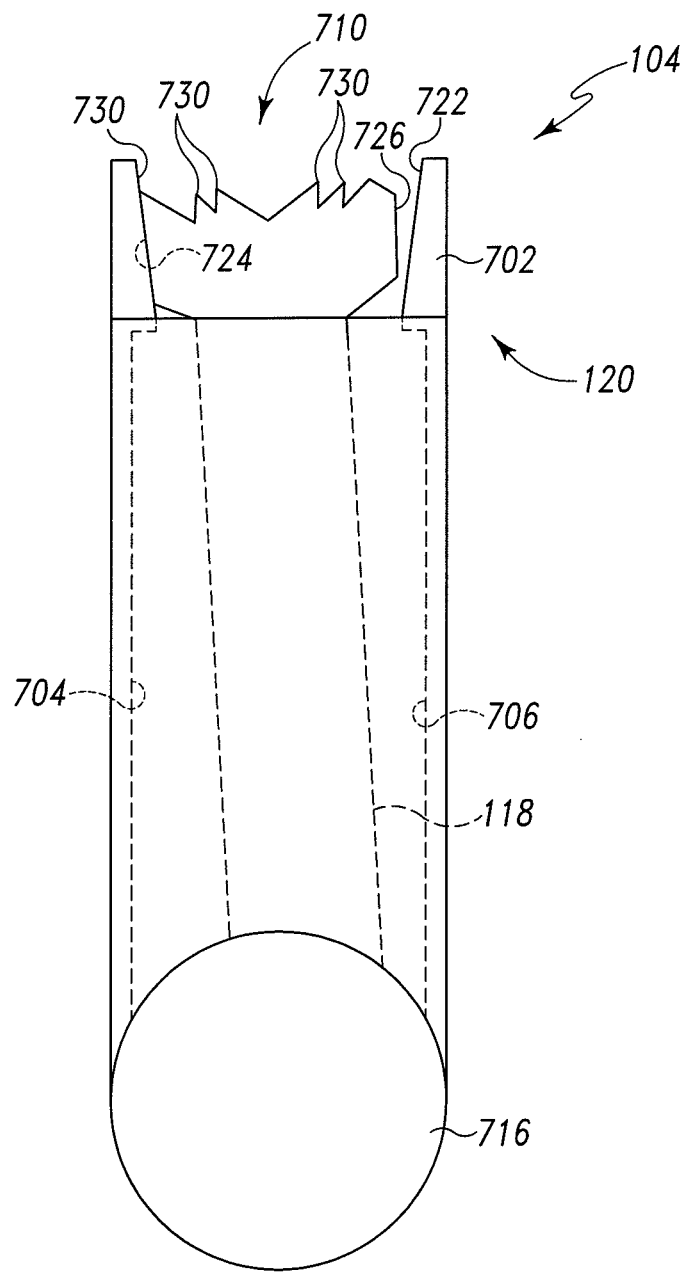
FIG. 35 is a top plan view of the of the bone saw blade assembly of FIG. 34 having the bone saw blade guard in an extended position.
Figure 36:
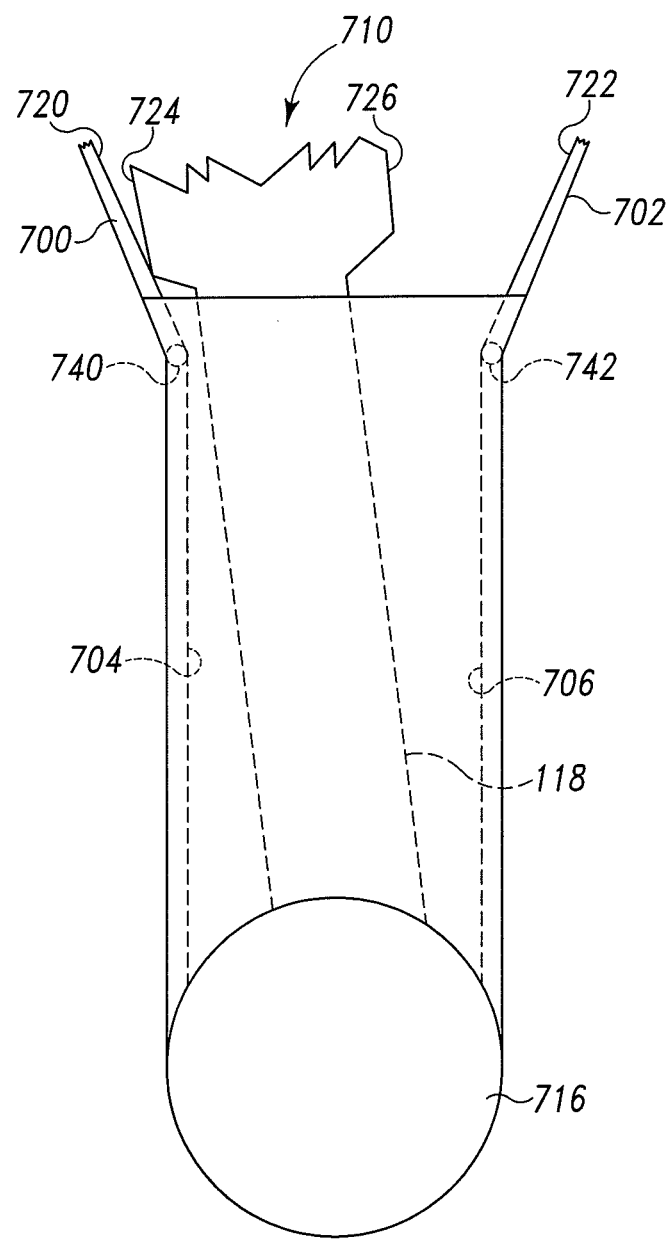
FIG. 36 is a top plan view of another embodiment of the bone saw assembly of FIG. 34 having the bone saw blade guard in an extended position.

Referring now to FIGS. 34-36, in another embodiment, the bone saw blade guard 120 is embodied as a pair of bumpers 700, 702. Each of the bumpers 700, 702 are coupled to corresponding push rods 704, 706, respectively. The bumpers 700, 702 and push rods 704, 706 are positioned on each side of the bone saw blade 118. The bone saw blade 118 and bone saw blade guard 120 (i.e., the bumpers 700, 702 and push rods 704, 706) are housed in a sleeve 708. The cutting end 710 of the bone saw blade 118 extends out of an end 712 of the sleeve 708 as shown in FIG. 34. As discussed in more detail below, the bumpers 700, 702 are located in the sleeve 708 in the retracted position and protrude from the sleeve 708 in the extended position.

The push rods 704, 706 are operatively coupled to a saw guard hub 716. The saw guard hub 716 is operable to extend and retract the push rods 704, 706 to thereby extend or retract the bumpers 700, 702. The bumpers 700, 702 and the push rods 704, 706 may be integral to or separate from each other. Illustratively, the bumpers 700, 702 have a substantially wedge shape including an inner angled side 720, 722 configured to contact a side 724, 726 of the bone saw blade 118 when in the extended position as shown in FIG. 35. The bumpers 700, 702 may be formed from any material sturdy enough to withstand contact of the bone saw blade 118 during operation. For example, in some embodiments, the bumpers 700, 702 are formed from a metallic material such that the bone saw blade 118 and the bumpers 700, 702 create an audible signal when the bumpers 700, 702 are in the extended position. Such audible signal may alert the surgeon that the bone saw blade guard 120 has been activated.

As illustrated in FIG. 34, when the bumpers 700, 702 are in the retracted position, the cutting teeth 730 of the bone saw blade 118 are exposed. As such, the bones saw blade 118 may be used to cut bone when the bumpers 700, 702 are in the retracted position. As discussed above, the bumpers 700, 702 may be moved to the extended position via the activation of the hub 716. That is, the hub 716 may be controlled to extend the push rods 704, 706, which in turn extend the bumpers 700, 702. As illustrated in FIG. 35, when the bumpers 700, 702 are moved to the extended position, the bumpers 700, 702 extend outwardly from the sleeve 708 a distance greater than the bone saw blade 118. Because the bumpers 700, 702 extend past the ends of the cutting teeth 730, the cutting teeth 730 are restricted from cutting. As such, when the bumpers 700, 702 are in the extended position, the ability of the bone saw blade 118 to cut bone is reduced or otherwise negated.

It should be appreciated that when the bumpers 700, 702 are in the extended position illustrated in FIG. 35, the movement of the bone saw blade 118 is restricted. That is, the radial movement of the bone saw blade 118 is restricted by the contact with the bumpers 700, 702, which causes the audible signal described above. However, in another embodiment illustrated in FIG. 36, the bumpers 700, 702 may be configured to swing outwardly when in the extended position such that the distance between the bumpers 700, 702 is increased in the extend position relative to the retracted position. The increased distance between the bumpers 700, 702 allows the bone saw blade 118 to maintain normal radial movement when the bumpers 700, 702 are extended. In such embodiments, the sleeve is flared toward the end 712 of the sleeve to allow the bumpers 700, 702 to swing outwardly from each other. Additionally, the bumpers 700, 702 are coupled to the push rods 704, 706 via hinges 740, 742, respectively.

Figures 37, 38:
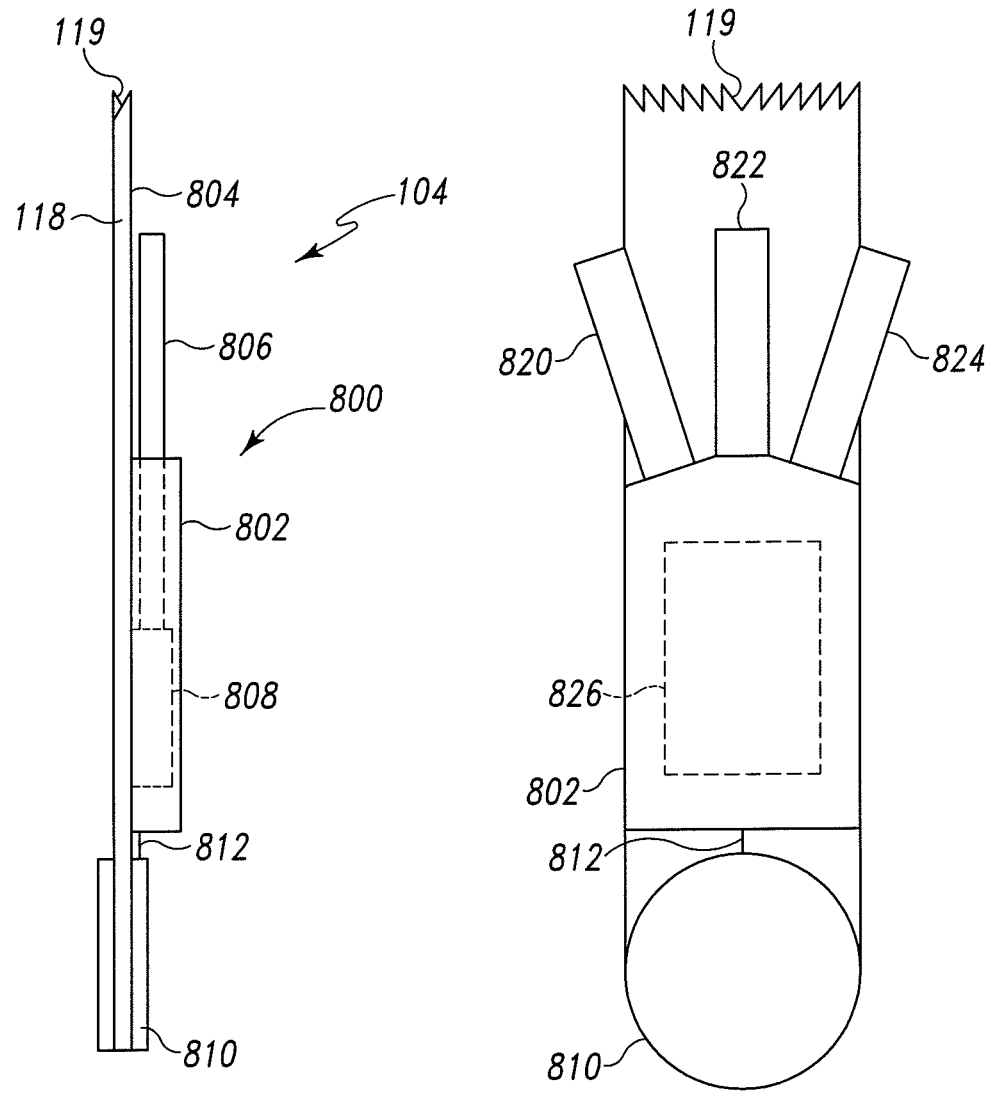
FIG. 37 is a side elevation view of another embodiment of the bone saw assembly of the bone saw tool of FIG. 6 including a cutting depth guard.
FIG. 38 is a bottom pan view of another embodiment of the bone saw assembly of FIG. 37.
Figure 39:
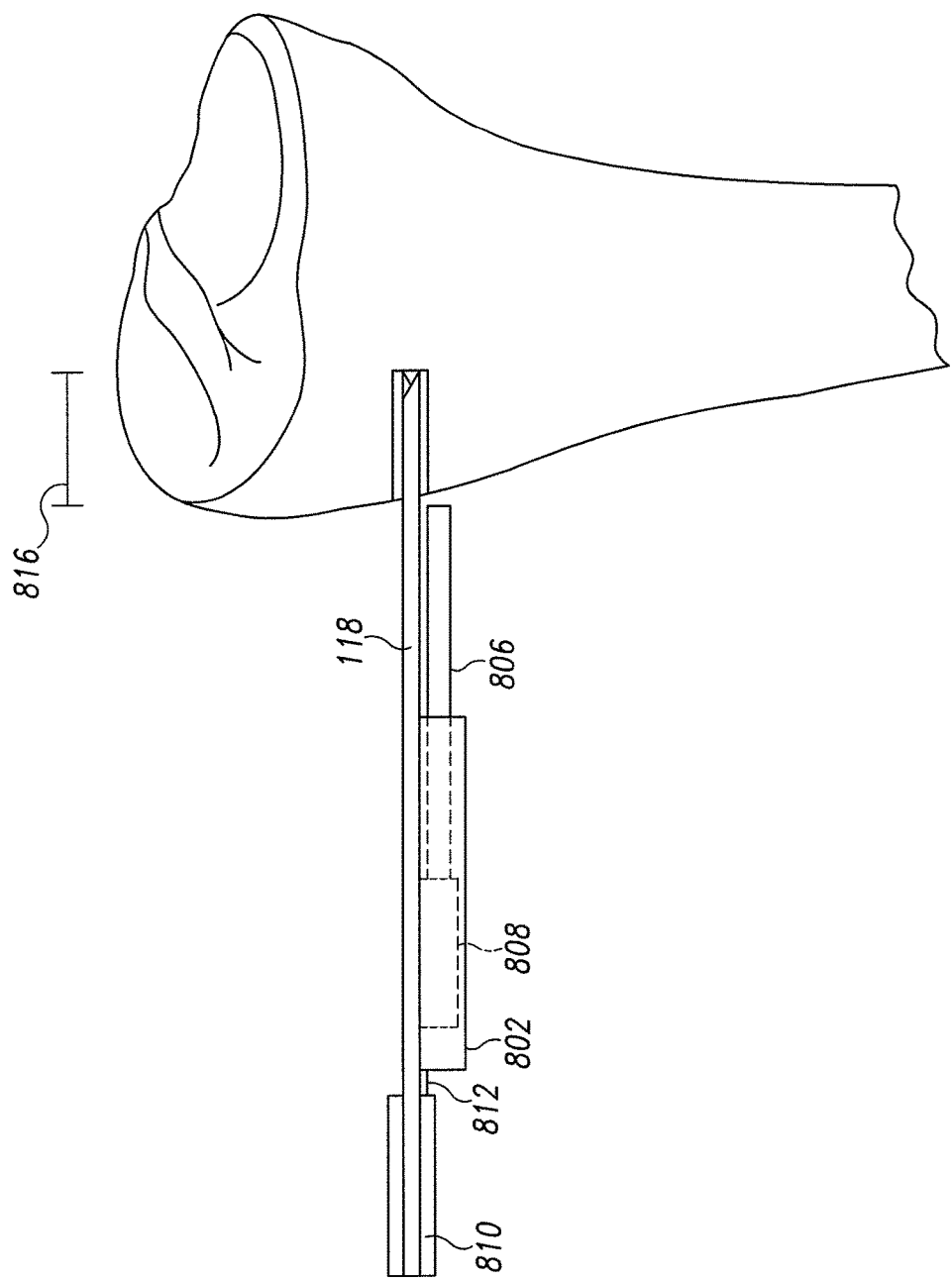
FIG. 39 is a side elevation view of the bone saw blade assembly of FIG. 37 during a bone resectioning procedure.

Referring now to FIGS. 37-39, in another embodiment, the bone saw blade assembly 104 may include a saw blade cutting depth guard 800. The cutting depth guard 800 includes a housing 802 secured to a bottom side 804 of the bone saw blade 118. A push rod 806 extends from the housing 802. The housing 802 includes an actuator 808 coupled to the push rod 806 and configured to extend or retract the push rod 806 relative to the housing 802. The actuator 808 may be communicatively coupled to a bone saw hub 810 via a communication link 812.

In use, the actuator 808 may be controlled to move the push rod 806 to a determined distance relative to a cutting end 814 of the bone saw blade 118. As such, the depth to which the bone saw blade 118 can cut is limited by the positioning of the push rod 806. For example, as shown in FIG. 39, the push rod 806 may be extend or retracted to selected position to define the maximum cutting depth 816 of the bone saw blade 118. The position of the push rod 806 may be preset or predetermined prior to the orthopaedic surgical procedure or may be positioned or repositioned during the orthopaedic surgical procedure based on, for example, the cutting speed, position of the bone saw blade 118, and/or the like.

In some embodiments, the cutting depth guard 800 may include any number of push rods. For example, as illustrated in FIG. 38, the cutting depth guard 800 may include three push rods 820, 822, 824, which extend from the housing 802. The push rods 820 and 824 are positioned at an angle relative to the centrally located push rod 822. Each of the push rods 820, 822, 824 may be separately extended from or retracted into the housing 802 via one or more actuators 826. As such, the cutting depth and radial cutting angle may be restricted or otherwise selected based on the positioning of the push rods 820, 822, 824.

Figure 40:
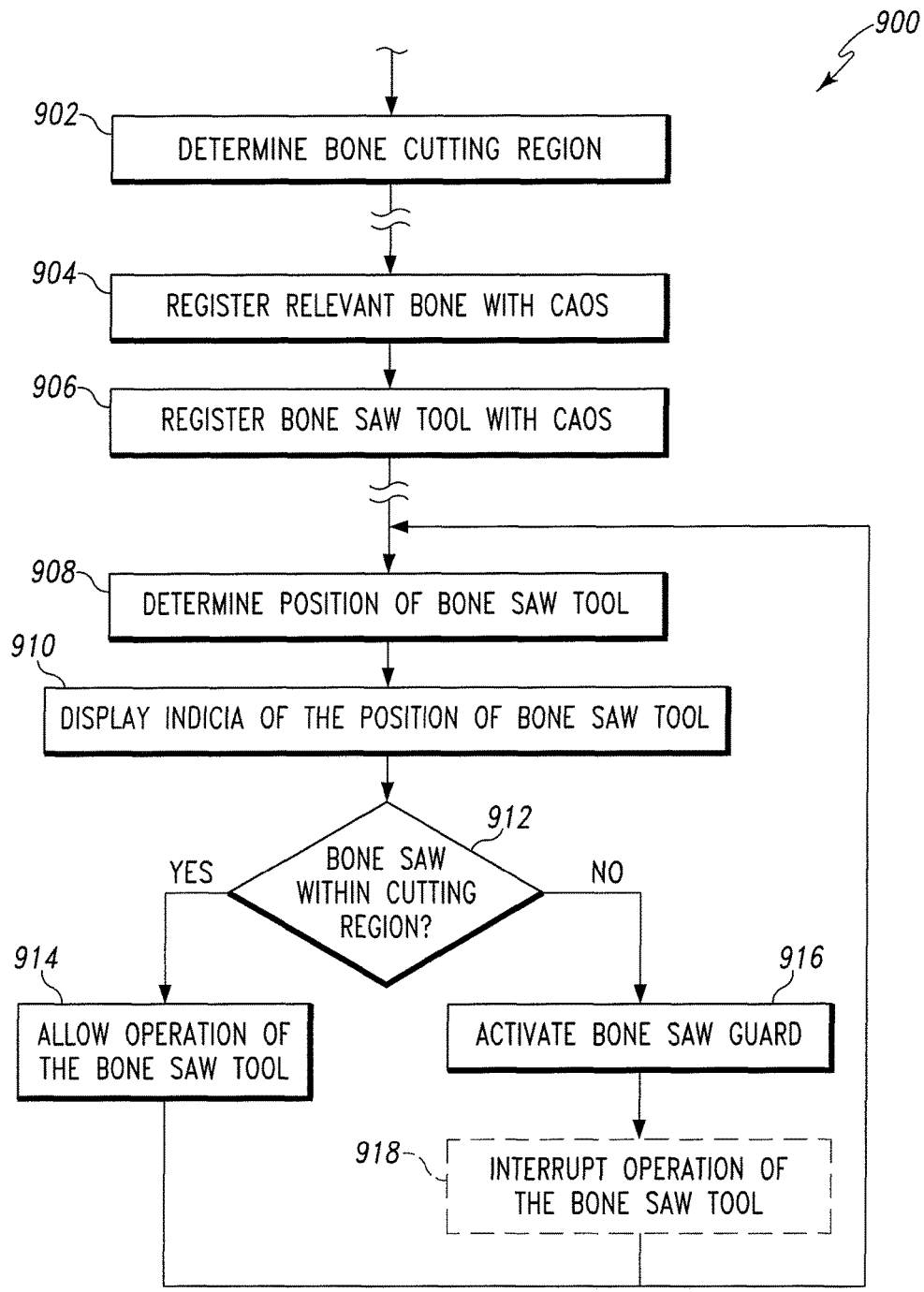
FIG. 40 is a flow diagram of a method for cutting a bone of a patient using a bone saw tool.

Referring now to FIG. 40, a method 900 for use with the bone saw tool 100 to cut a bone of a patient during the performance of an orthopaedic surgical procedure begins with a process step 902. In process step 902, the bone cutting region of the relevant bone of the patient is determined. The cutting region corresponds to the volume of bone to be removed from the patient. For example, in a total knee arthroscopy procedure, the cutting region may correspond to a portion of the medial and lateral condyles of the patient's femur. The cutting region may be determined based on previously generated medical images such as X-rays or the like.

Once the cutting region has been determined in process step 902, the surgeon may begin the orthopaedic surgical procedure. To do so, in process step 904, the relevant bone of the patient (i.e., the bone to be cut) is registered with the computer assisted orthopaedic surgery system 10. To do so, the surgeon may couple a reference array to the relevant bone and use a registration pointer, such as the registration point 80 illustrated in and described above in regard to FIG. 4, to register the contours of the relevant bone with the computer assisted orthopaedic surgery system 10. Subsequently in process step 906, the bone saw tool 100 is registered with the computer assisted orthopaedic surgery system 10 using the reference array 106 coupled thereto. The bone saw tool 100 may be registered with the system 10 in a manner similar to other orthopaedic surgical tools.

Once the relevant bone and bone saw tool 100 have been registered with the computer assisted orthopaedic surgery system 10, the position of the bone saw tool 100 is determined in process step 908. To do so, the computer 12 receives data from the camera unit 14, 16 or other sensory device configured to operate with the reference array 106 of the bone saw tool 100. The computer 12 determines the position of the bone saw tool 100 within the coordinate system 108 (see FIG. 6) based on such data in a manner as described above in regard to FIGS. 1-5. Once the position of the bone saw tool 100 has been determined by the computer 12, the computer 12 displays indicia of the bone saw tool 100 on the display 44 in a position and orientation based on the data received from the sensory device (e.g., from the camera unit 14, 16).

Subsequently, in process step 912, the computer 12 determines if the bone saw tool 100 is within the cutting region as determined in process step 202. To do so, the computer is configured to compare the location of the bone saw tool 100 as determined in process step 908 to the cutting region. If the computer 12 determines that the bone saw tool 100 is within the cutting region, the algorithm 900 advances to process step 914 wherein the computer 12 allows the operation of the bone saw tool 100. That is, the bone saw tool 100 may be used by the surgeon to cut the relevant bone of the patient in process step 914.

However, if the computer 12 determines that the bone saw tool 100 is outside the cutting region as determined in process step 902, the computer 12 activates the bone saw guard 120 (or the cutting depth guard 800) of the bone saw tool 100 in process step 916. To do so, the computer 12 may transmit a signal to the bone saw tool 100 via the communication link 112. In response, the bone saw 102 of the bone saw tool 100 activates the guard actuator 116 to cause the bone saw blade guard 120 (or the cutting depth guard 800) to be moved to the extended position such that the cutting effectiveness of the bone saw blade 118 is reduced. That is, the guard actuator 116 and the saw guard hub(s) cooperate to move the bone saw blade guard 120 to the extended position.

In some embodiments, the bone saw 102 may also be configured to stop operation in process step 918 when the bone saw tool 100 is not within the cutting region. That is, if the bone saw tool 100 receives the signal from the computer 12 indicating that the bone saw tool 100 is no longer within the cutting region, the bone saw 102 is configured to halt the bone saw blade 118 or otherwise stop oscillating the blade 118. In this way, the operation of the bone saw 102 is halted and the bone saw guard 120 is activated whenever the bone saw tool 100 is outside the cutting region.

Figure 41:
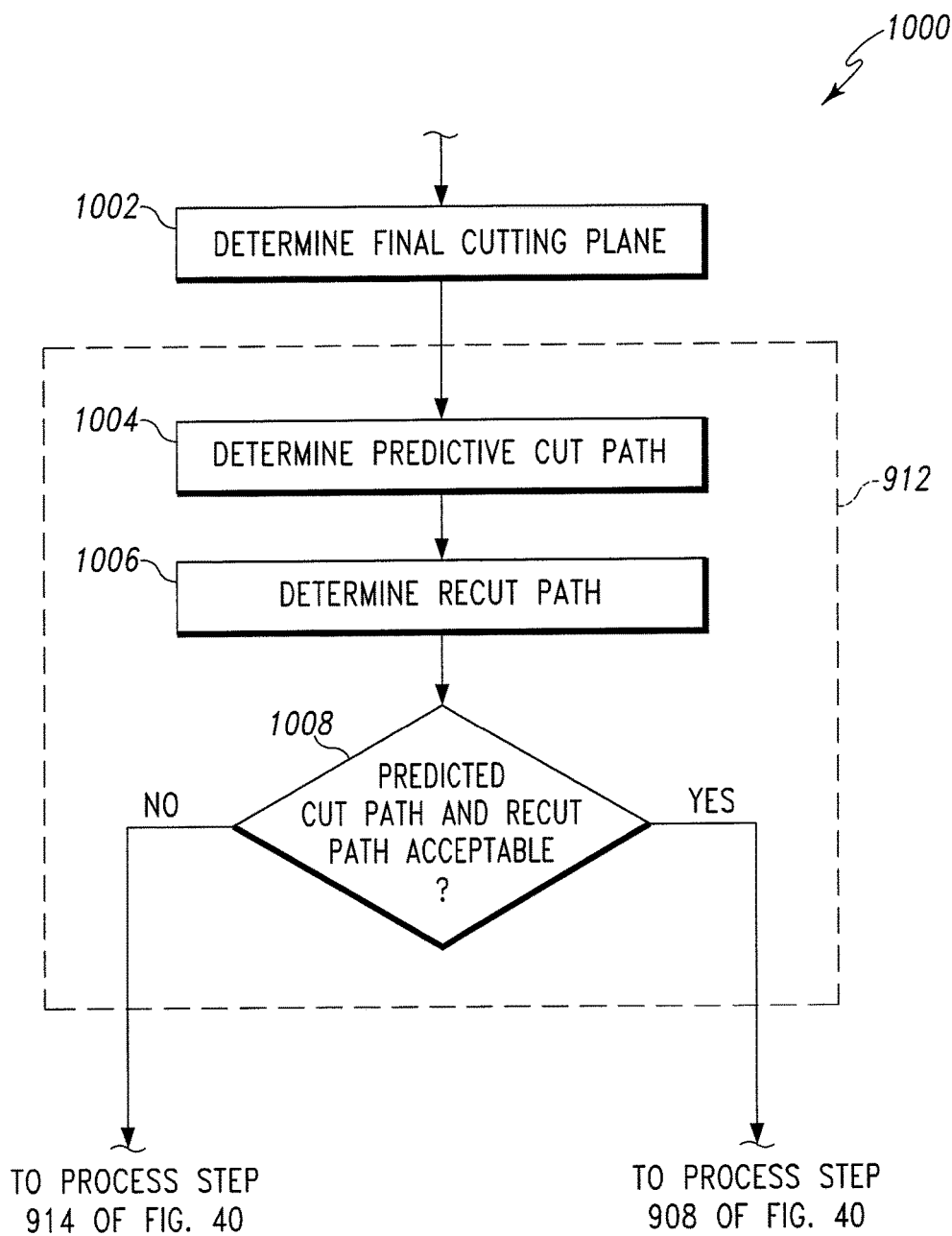
FIG. 41 is a flow diagram of a sub-method of the method of FIG. 40 for determining whether the bone saw tool is within a cutting region.

A number of different algorithms may be used to determine whether the bone saw tool 100 is within the cutting region in step 912 of the method 900 described above in regard to FIG. 40. For example, in one embodiment, a method 1000 for predicting and verifying the cutting plane of the bone saw tool 100 may be used as shown in FIG. 41. The method 1000 beings with a process step 1002 in which the final cutting plane of the relevant bone of the patient is determined. The final cutting plane may be determined as a sub-step in process step 902 of method 900 in which the cutting region is determined. The final cutting plane corresponds to the resectioning plane of the patient's bone along which the bone saw blade 118 should cut to remove the desired volume of bone. The final cutting plane may be based on previously generated medical images such as X-rays or the like.

Figure 42:
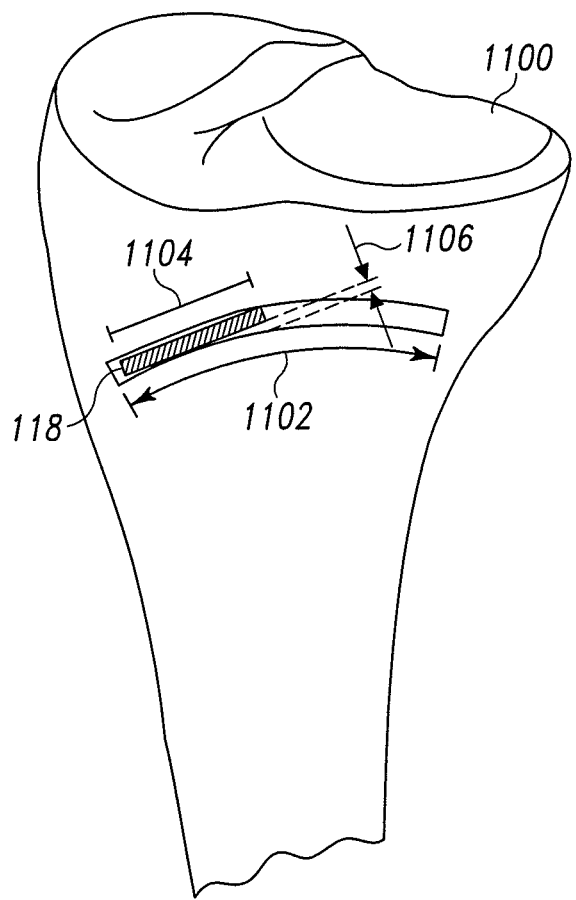
FIG. 42 is a perspective view of a bone saw blade of a bone saw tool during operation.

The computer assisted orthopaedic surgery system 10 may be configured to prompt or otherwise inform the surgeon to being the bone cutting process above the desired final cutting plane to ensure too much bone is not inadvertently removed. Such a starting point allows the system 10 to predict the movement of the bone saw blade 118 to monitor whether the surgeon is on a valid cutting path. To do so, in process step 1004, the computer assisted orthopaedic system 10 predicts the cut path of the bone saw blade 118 of the bone saw tool 100 based on, for example, the minimum cutting turning radius of the bone saw blade 118. For example, as illustrated in FIG. 42, the minimum turning radius 1102 of the bone saw blade 118 may be determined based on the width 1104 of the bone saw blade 118 and the clearance distance 1106 of the bone saw blade 118. The clearance distance 1106 may be based on the width 1104 of the bone saw blade 118 and is an estimation of the amount of bone material removed by the teeth of the bone saw blade 118. For example, a bone saw blade 118 having a width 1104 of about 20 millimeters may have a clearance distance 1106 of about 0.24 millimeters. A bone saw blade 118 having a width 1104 of about 75 millimeters may have a clearance distance 1106 of about 3 millimeters. The minimum turning radius 1102 may be determined based on the following equation:

$$mRadius = (Width^2 - \delta Saw^2)/2*\delta Saw$$

wherein "mRadius" is the minimum turning radius 1102, "Width" is the width 1104 of the bone saw blade 118, and "δSaw" is the clearance distance 1106. Based on the calculated minimum turning distance 1102, the computer assisted orthopaedic system 10 is able to predict the cutting path of the bone saw blade 118 and compare such cutting path to the final cutting path as discussed in more detail below. It should be appreciated that the above equation may be used to determine the lateral deviation of the bone saw blade 118. Similar calculations may be used to determine the axial deviation of the bone saw blade 118. In such calculations, the width 1104 of the bone saw blade 118 is replaced by the variable distance to which the bone saw blade 118 penetrates into the patient's bone 1100.

In process step 1006, the computer assisted orthopaedic system 10 determines the required recut path of the bone saw blade 118 to achieve the final cutting plane based on the cutting path determined in process step 1004. The minimum turning radius 1102 may also be considered in determining the required recut path.

In process step 1108, the computer assisted orthopaedic system 10 compares the cutting path of the bone saw blade 118 calculated in step 1004 to the final cutting path determined in process step 1002. If calculated cutting path of the bone saw blade 118 results in a cutting plane below the final cutting plane determined in process step 1002, the method 1000 advances to step 916 of method 900 (see FIG. 40), in which the bone saw blade guard 120 is activated or otherwise the cutting effectiveness of the cutting teeth of the bone saw blade 118 is reduced. However, if the calculated cutting path is above or at the final cutting plane, the method 1000 advances to step 914 in which the computer assisted orthopaedic surgery system 10 allows the operation of the bone saw tool 100. In addition to comparing the cutting path of the bone saw blade 118 determined in step 1104 to the final cutting path, the system 10 determines whether the recut path determined in step 1006 is acceptable to achieve the final cut plane determined in process step 1002. If so, the method 1000 advances to step 914. However, if the required recut path is unacceptable (e.g., the recut path requires a minimum turning radius less than that achievable with the bone saw blade 118), the method 1000 advances to step 916 as discussed above.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A method for cutting a bone of a patient using a bone saw tool having a bone saw blade with a plurality of cutting teeth, the method comprising:
   determining a cutting region within a coordinate system defined by a computer assisted orthopaedic surgery system, the cutting region corresponding to a region of the bone to be cut;
   determining the position of the bone saw tool in the coordinate system;
   determining whether the bone saw tool has exited the cutting region defined in the coordinate system; and
   activating a bone saw blade guard of the bone saw tool based on a determination that the bone saw tool has exited the cutting region, the bone saw blade guard being devoid of any cutting teeth,
   wherein activating the bone saw blade guard comprises extending a plurality of slats of the bone saw blade guard with respect to the bone saw blade to cover a portion of the bone saw blade, each slat being positioned in a slot defined in the bone saw blade between each cutting tooth of the plurality of cutting teeth of the bone saw blade.

2. The method of claim 1, wherein activating the bone saw blade guard comprises reducing the cutting effectiveness of the bone saw blade of the bone saw tool.

3. The method of claim 1, wherein activating the bone saw blade guard comprises covering at least a portion of the cutting teeth of the bone saw blade with the bone saw blade guard.

4. The method of claim 1, wherein extending the plurality of slats further comprises:
   advancing a first slat positioned over a first side of the bone saw blade of the bone saw tool such that the first slat covers a portion of the cutting teeth of the bone saw blade on the first side; and advancing a second slat positioned over a second side of the bone saw blade such that the second slat covers a portion of the cutting teeth of the bone saw blade on the second side.

5. The method of claim 1, further comprising reducing the movement of the bone saw blade of the bone saw tool if the bone saw tool is outside the cutting region.

6. The method of claim 1, wherein each slat is coplanar with the bone saw blade.

7. The method of claim 1, wherein activating the bone saw blade guard further comprises extending a rod positioned in an inner passageway defined in the bone saw blade.

8. A method for cutting a bone of a patient using a bone saw tool having a bone saw blade with a plurality of cutting teeth, the method comprising:

determining a cutting region within a coordinate system defined by a computer assisted orthopaedic surgery system, the cutting region corresponding to a region of the bone to be cut;

determining the position of the bone saw tool in the coordinate system;

determining whether the bone saw tool has exited the cutting region defined in the coordinate system; and reducing the cutting effectiveness of the cutting teeth of the bone saw blade of the bone saw tool based on a determination that the bone saw tool has exited the cutting region, wherein reducing the cutting effectiveness of the cutting teeth comprises activating a bone saw blade guard, the bone saw blade guard being devoid of any cutting teeth, wherein activating the bone saw blade guard comprises extending a plurality of slats of the bone saw blade guard positioned coplanar with the bone saw blade such that the plurality of slats extend beyond the cutting teeth of the bone saw blade, and wherein reducing the cutting effectiveness of the cutting teeth comprises altering the thickness of a bone saw blade assembly of the bone saw tool.

9. The method of claim 8, wherein reducing the cutting effectiveness of the cutting teeth further comprises reducing a depth to which the bone saw blade is able to penetrate the bone of the patient.

* * * * *